United States Patent
Brouillette et al.

(10) Patent No.: US 6,509,359 B1
(45) Date of Patent: Jan. 21, 2003

(54) PYRROLIDIN-2-ONE COMPOUNDS AND THEIR USE AS NEURAMINIDASE INHIBITORS

(76) Inventors: Wayne J. Brouillette, 328 Kings Crest La., Pelham, AL (US) 35124; Venkatram Reddy Atigadda, 1735 Ski Lodge III, Birmingham, AL (US) 35209; Ming Luo, 1659 Crossgate Dr., Vestavia Hills, AL (US) 35216; Yarlagadda S. Babu, 3441 Strollway Dr., Birmingham, AL (US) 35226

( * ) Notice: Subject to any disclaimer, the term of this patent is extended or adjusted under 35 U.S.C. 154(b) by 0 days.

(21) Appl. No.: 09/527,189

(22) Filed: Mar. 17, 2000

Related U.S. Application Data

(63) Continuation-in-part of application No. PCT/US99/19298, filed on Sep. 17, 1998
(60) Provisional application No. 60/059,326, filed on Sep. 17, 1997.

(51) Int. Cl.[7] .................. A61K 31/4418; C07D 207/27; C07D 211/76
(52) U.S. Cl. ............. 514/327; 514/210.02; 514/211.03; 514/423; 514/424; 514/428; 540/200; 540/531; 546/24; 546/221; 546/243; 548/413; 548/541; 548/543; 548/551
(58) Field of Search ................................. 514/423, 428, 514/424, 210.02, 211.03, 327; 548/543, 551, 541, 413; 540/200, 531; 546/24, 221, 243

(56) References Cited

U.S. PATENT DOCUMENTS

| | | |
|---|---|---|
| 3,666,746 A * | 5/1972 | Stanley et al. ............... 260/152 |
| 3,717,659 A | 2/1973 | Sarett et al. ............. 260/326.3 |
| 5,453,533 A | 9/1995 | Luo et al. .................... 560/142 |
| 5,512,596 A | 4/1996 | Kim et al. .................. 514/568 |
| 5,602,277 A | 2/1997 | Babu et al. ................. 562/439 |

FOREIGN PATENT DOCUMENTS

WO    WO 99/14191    3/1999

OTHER PUBLICATIONS

Kukalenko et al., Structure and hydrolysis of p-(2-oxo-1-pyrrolidinyl)benzenesulfonic acid, 1987, Zh. Obshch. Khim., 57 (6), 1265–70.*

N-Aryl-α-pyrrolidinones, *Chemical Abstracts* 52, 1958: 11124, Hopff et. al.

* cited by examiner

*Primary Examiner*—Ceila Chang
*Assistant Examiner*—Sonya Wright
(74) *Attorney, Agent, or Firm*—Connolly Bove Lodge & Hutz LLP

(57) ABSTRACT

A compound having the formula:

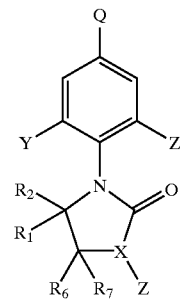

wherein all variables are as defined in the specification, for use as a neuramninidase inhibitor.

42 Claims, No Drawings

PYRROLIDIN-2-ONE COMPOUNDS AND THEIR USE AS NEURAMINIDASE INHIBITORS

CROSS REFERENCE

This application is a continuation-in-part of PCT Application Serial No. PCT/US98/19298 filed Sep. 17, 1998 which claims priority from Provisional Application Serial No. 60/059,326 filed Sep. 17, 1997, both of which are incorporated by reference in their entirety for all purposes.

DESCRIPTION

1. Technical Field

This invention relates to novel pyrrolidin-2-one derivatives, their use as neuraminidase inhibitors, to pharmaceutical compositions containing these novel compounds useful for the prevention, treatment or amelioration of viral, bacterial and other infections, and to methods of using the compounds. The present invention is also concerned with novel intermediates or precursors for producing the novel pyrrolidin-2-one compounds of the present invention.

2. Background of the Invention

Despite the wealth of the information available, influenza remains a potentially devastating disease of man, lower mammals, and birds. No effective vaccine exists and no cure is available once the infection has been initiated.

Influenza viruses consist of eight pieces of single stranded RNA, packaged in orderly fashion within the virion. Each piece codes for one of the major viral proteins. The replication complex is enclosed with a membrane composed of matrix proteins associated with a lipid bilayer. Embedded in the lipid bilayer are two surface glycoprotein spikes, hemagglutinin (HA) and the enzyme neuraminidase (NA). All of the viral genes have been cloned and the three-dimensional structures of the surface glycoproetins have been determined.

Influenza viruses continually undergo variation in the two surface antigen, HA and NA, toward which neutralizing antibodies are directed. For this reason, vaccines and a subject's natural immune system have not been very effective. Attention is now being directed to finding other potential antiviral agents acting at other sites of the virion. This invention is directed to novel compounds which are useful in inhibiting the viral surface enzyme NA.

Furthermore, many other organisms carry NA. Many of these NA-possessing organisms are also major pathogens of man and/or mammals, including *Vibraeo cholerae, Clostridium perfringes, Streptococcus pneumonia, Arthrobacter sialophilas*, and other viruses, such as parainfluenza virus, mumps virus, Newcastle disease virus, fowl plague virus, and Sendai virus. Compounds of this invention are also directed to inhibiting NA of these organisms.

In viruses, NA exists as a tetramer made of four roughly spherical subunits and a centrally-attached stalk containing a hydrophobic region by which it is embedded in the organism's membrane. Several roles have been suggested for NA. The enzyme catalyzes cleavage of the α-ketosidic linkage between terminal sialic acid and an adjacent sugar residue. Removal of the sialic acid lowers the viscosity and permits access of the virus to the epithelial cells. NA also destroys the HA receptor on the host cell, thus allowing elution of progency virus particles from infected cells. Research indicates that the active site for influenza neuraminidase remains substantially unchanged for the major strains of influenza. For example, a comparison of sequences from influenza A subtypes and influenza B shows conserved residues with crucial structural and functional roles. Even though the sequence homology is only about 30%, many of the catalytic residues are conserved. Furthermore, the three-dimensional structures of influenza A and B neuraminidases have been determined. Superposition of the various structures shows remarkable structural similarity of the active site. Since the active site amino acid residues are conserved in all known influenza. A neuraminidases that have been sequenced so far, an inhibitor that is effective against different strains of influenza A and/or B neuraminidase can be designed based on the three-dimensional structure of a neuraminidase.

In general, the role of NA is thought to be for the mobility of the virus both to and from the site of infections. Compounds that inhibit neuraminidase's activity may protect a subject from infection and/or cure a subject once infection has set in. It is a further object of this invention to provide a method of using compounds of this invention for preventing, treating and/or curing a viral infection.

Analogs of neuraminic acid, such as 2-deoxy-2,3-didehydro-N-acetylneuraminic acid (DANA) and its derivatives are known to inhibit HA in vitro; however, these compounds are inactive in vivo. Palese and Schulman, in CHEMOPROPHYLAXIS AND VIRUS INFECTION OF THE UPPER RESPIRATORY TRACT, Vol. 1 (J. S. Oxford, Ed.), CRC Press, 1977, at pp. 189–205.

Von Itzstein et al. Describes cyclohexane analogs of α-D-neuraminic acid of the formula

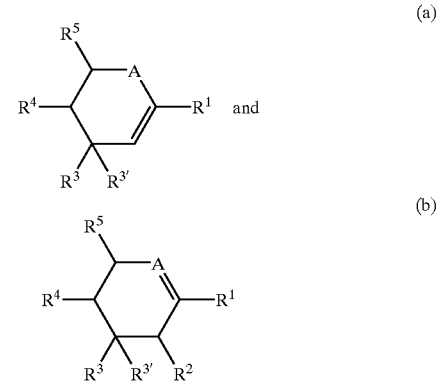

wherein:
  A is O, C or S in Formula (a), and N or C in Formula (b);
  $R^1$ is $CO_2H$, $PO_3H_2$, $NO_2$, $SO_2H$, $SO_3H$, tetrazolyl-, $CH_2CHO$, CHO, or $CH(CHO)_2$; $R^2$ is H, $OR^6$, F, Cl, Br, CN, $NHR^6$, $SR^6$ or $CH_2X$, where X is $NHR^6$ halogen, or $OR^6$;
  $R^3$ and $R^{3'}$ are H, CN, $NHR^6$, $SR^6$, $=NOR^6$, $OR^6$, guanidino, $NR^6$;
  $R^4$ is $NHR^6$, $SR^6$, $OR^6$, $CO_2R^6$, $NO_2$, $C(R^6)_3$, $CH_2CO_2R^6$, $CH_2$ or $CH_2NHR^6$;
  $R^5$ is $CH_2YR^6$, $CHYR^6CH_2YR^6$ or $CHYR^6CHYR^6CH_2YR^6$;
  $R^6$ is H, acyl, alkyl, allyl, or aryl;
  Y is O, S, NH, or H;
and pharmaceutical salts thereof, useful as antiviral agents.

In addition, certain benzene derivatives are suggested in U.S. Pat. No. 5,453,533 as being inhibitors of influenza virus neuraminidase and various others are disclosed in U.S. patent application ser. No. 08/413,886. Yamamoto et al. Describe various sialic acid isomers as having inhibitory activity against neuraminidase in Synthesis of Sialic Acid Isomers Inhibitory Activity Against Neuraminidase, TETRAHEDRON LETTERS, Vol. 33, No. 39, pp. 5791–5794, 1992.

U.S. Pat. No. 5,512,596 and WO 96/26933 to Gilead Sciences, Inc. describes certain 6-membered ring compounds as possible inhibitors of neuraminidase.

Hoff, et al. Suggests that certain N-aryl α-pyrrolidinones are useful as intermediates for dyes and pharmaceuticals, as reported in *Chemical Abstracts*, Vol. 52, Item 11124 g, 1958.

However, none of these references disclose the novel pyrrolidin-2-one derivatives of the present invention.

SUMMARY OF THE INVENTION

An aspect of the present invention is directed to compounds represented by the formula:

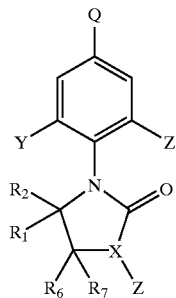

wherein

Q is $CO_2H$, $SO_3H$, $PO_3H_2$, $NO_2$ or esters thereof;

Y is H, OH, $NH_2$, $CH_2\overset{NH_2}{\underset{|}{C}}=NH$, $CH_2\overset{NOH}{\underset{\|}{C}}NH_2$ or $NH\overset{NH}{\underset{\|}{C}}NH_2$ Z is H, $(CH_2)nNH\overset{NR_3}{\underset{\|}{C}}NR_4R_5$, $(CH_2)nNHCHR_3R_4$, $(CH_2)nNR_3R_4$, $(CH_2)nN\overset{O}{\underset{\|}{R_3C}}R_4$, $(CH_2)nOR_3$, $(CH_2)nO\overset{O}{\underset{\|}{C}}R_3$, $(CH_2)nR_3$, $(CH2)nCH_2CHR_3R_4$, $(CH_2)nCH_2\overset{R_4}{\underset{|}{C}}H\overset{R_5}{\underset{|}{C}}H(CH_2)nT$, $(CH_2)n\overset{O}{\underset{\|}{C}}NR_3R_4$ or $(CH_2)n\overset{O}{\underset{\|}{C}}NHCHR_3R_4$;

T is H, OH or $OH_2$
n is 0–3;
X is $(CH_2)n$, $(CH_2)nNH$, $(CH_2)nO$ or $(CH_2)nS$;
Each of $R_1$ and $R_2$ individually is H, $(CH_2)mA$, or $(CH_2)mZ$, and $R_1$ and $R_2$ can be the same or different;
Each of $R_6$ and $R_7$ individually is H, $(CH_2)mA$, or $(CH_2)mZ$, and $R_6$ and $R_7$ can be the same or different;
m is 1–3;

A is OH, $NH_2$, CN, $CONH_2$, $\overset{NH_2}{\underset{|}{C}}=NH$ or $NH\overset{NH_2}{\underset{|}{C}}=NH$;

each of $R_3$, $R_4$, $R_5$ individually is H, lower alkyl, branched alkyl, cycloalkyl, aryl or alkaryl, and $R_3$, $R_4$ and $R_5$ can be the same as or can differ from each other; and pharmaceutically acceptable salts thereof.

The present invention is also concerned with compositions for inhibiting influenza virus neuraminidase comprising a pharmaceutically acceptable carrier and an amount effective for inhibiting influenza virus neuraminidase of a compound as defined above.

A further aspect of the present invention involves a method for inhibiting influenza virus that comprises administering to a patient in need thereof a compound as defined above in an amount effective for inhibiting influenza virus neuraminidase.

A still further aspect of the present invention is concerned with preventing and treating influenza virus infection comprising administering to a patient in need thereof a compound as defined above in an amount effective for inhibiting influenza virus neuraminidase.

The present invention is also concerned with methods for producing the compounds defined above.

Still other objects and advantages of the present invention will become readily apparent by those skilled in the art from the following detailed description, wherein it is shown and described only the preferred embodiments of the invention, simply by way of illustration of the best mode contemplated of carrying out the invention. As will be realized, the invention is capable of other and different embodiments, and its several details are capable of modifications in various obvious respects, without departing from the invention. Accordingly, the description is to be regarded as illustrative in nature and not as restrictive.

Best and Various Modes for Carrying Out Invention

An aspect of the present invention is directed to compounds represented by the formula:

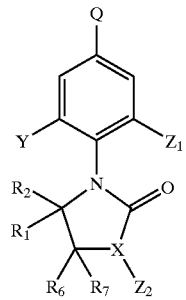

wherein

Q is $CO_2H$, $SO_3H$, $PO_3H_2$, $NO_2$ or esters thereof;

Y is H, OH, $NH_2$, $CH_2\overset{NH_2}{\underset{|}{C}}=NH$, $CH_2\overset{NOH}{\underset{\|}{C}}NH_2$ or $NH\overset{NH}{\underset{\|}{C}}NH_2$ $Z_1$ and $Z_2$ are H, $(CH_2)nNH\overset{NR_3}{\underset{\|}{C}}NR_4R_5$, $(CH_2)nNHCHR_3R_4$, $(CH_2)nNR_3R_4$, $(CH_2)nN\overset{O}{\underset{\|}{R_3C}}R_4$, $(CH_2)nOR_3$, $(CH_2)nO\overset{O}{\underset{\|}{C}}R_3$, $(CH_2)nR_3$, $(CH2)nCH_2CHR_3R_4$, $(CH_2)nCH_2\overset{R_4}{\underset{|}{C}}H\overset{R_5}{\underset{|}{C}}H(CH_2)nT$, $(CH_2)n\overset{O}{\underset{\|}{C}}NR_3R_4$ or $(CH_2)n\overset{O}{\underset{\|}{C}}NHCHR_3R_4$;

T is H, OH or $OH_2$
n is 0–3;

X is (CH$_2$)n, (CH$_2$)nNH, (CH$_2$)nO or (CH$_2$)nS;

Each of R$_1$ and R$_2$ individually is H, (CH$_2$)mA, or (CH$_2$)mZ, and R$_1$ and R$_2$ can be the same or different;

Each of R$_6$ and R$_7$ individually is H, (CH$_2$)mA, or (CH$_2$)mZ, and R$_6$ and R$_7$ can be the same or different; m is 1–3;

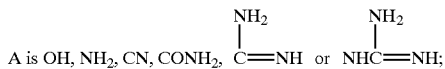

A is OH, NH$_2$, CN, CONH$_2$, C=NH or NHC=NH;

each of R$_3$, R$_4$ R$_5$ individually is H, lower alkyl, branched alkyl, cycloalkyl, aryl or alkaryl, and R$_3$, R$_4$ and R$_5$ can be the same as or can differ from each other; and pharmaceutically acceptable salts thereof.

The esters are typically lower alkyl esters having 1 to about 12 carbon atoms and preferably 1 to about 3 carbon atoms and aryl esters containing 6 to 14 carbon atoms. The alkyl esters can be straight-chain, branched-chain or cyclic saturated aliphatic hydrocarbons.

Examples of some alkyl esters are methyl, ethyl, propyl, isopropyl, t-butyl, cyclopentyl and cyclohexyl esters. The aryl esters are preferably phenyl or alkyl substituted aromatic esters (alkaryl) including C$_{1-3}$ alkyl substituted phenyl such as benzyl.

The alkyl groups contain 1 to about 12 carbon, and preferably 1 to about 3 carbon atoms, and can be straight, branched-chain or cyclic saturated aliphatic hydrocarbon groups.

Examples of suitable alkyl groups include methyl, ethyl and propyl. Examples of branched alkyl groups include isopropyl and t-butyl. Examples of suitable cyclic aliphatic groups typically contain 3–8 carbon atoms and include cyclopentyl and cyclohexyl.

Examples of substituted cycloalkyl groups include cyclic aliphatic groups typically containing 3–8 carbon atoms in the ring substituted with alkyl groups typically having 1–6 carbon atoms and/or hydroxy group. Usually 1 or 2 substituted groups are present.

Examples of aryl groups are phenyl and naphthyl. Alkaryl groups typically contain 1–3 carbon atoms in the alkyl group such as benzyl. The alkyl moiety can be linear or branched.

Pharmaceutically acceptable salts of the compounds of formula (I) include those derived from pharmaceutically acceptable, inorganic and organic acids and bases. Examples of suitable acids include hydrochloric, hydrobromic, sulphuric, nitric, perchloric, fumaric, maleic, phosphoric, glycollic, lactic, salicyclic, succinic, toluene-p-sulphonic, tartaric, acetic, citric, methanesulphonic, formic, benzoic, malonic, naphthalene-2-sulphonic, trifluoroacetic and benzenesulphonic acids.

Salts derived from appropriate bases include alkali such as sodium and ammonia.

Examples of some specific compounds within the scope of the present invention are:

1-{2-{[(Amino)(imino)methyl]amino}-4-carboxyphenyl}pyrrolidin-2-one;

1-{2-{[(Amino)(imino)methyl]amino}-4-carboxyphenyl}-5-(hydroxymethyl)pyrrolidin-2-one;

1-{2-{[(Amino)(imino)methyl]amino}-4-carboxyphenyl}-5-(aminomethyl)pyrrolidin-2-one;

1-(4-Carboxyphenyl)-5,5-bis-(hydroxymethyl)pyrrolidin-2-one;

1-{2-{[(Amino)(imino)methyl]amino}-4-carboxyphenyl}-5,5-bis-(hydroxymethyl)pyrrolidin-2-one;

1-{4-Carboxy-2-(3-pentylamino)phenyl]pyrrolidin-2-one;

1-[4-Carboxy-2-(3-pentylamino)phenyl]-5,5-bis-(hydroxymethyl)pynolidin-2-one;

1-[4-Carboxy-2-(3-hexylamino)phenyl]-5,5-bis-(hydroxymethyl)pyrrolidin-2-one;

1-[4-Carboxy-2-(4-heptylamino)phenyl]-5,5-bis-(hydroxymethyl)pyrrolidin-2-one;

1-{4-Carboxy-2-[(3-pentyl)methylamino)phenyl}-5,5-bis-(hydroxymethyl)pyrrolidin-2-one;

1-[4-Carboxy-2-(propylamino)phenyl]-5,5-bis-(hydroxymethyl)pyrrolidin-2-one;

1-[4-Carboxy-2-(pentylamino)phenyl]-5,5-bis-(hydroxymethyl)pyrrolidin-2-one;

1-[4-Carboxy-2-(ethylcarbonylamino)phenyl]-5,5-bis-(hydroxymethyl)pyrrolidin-2-one;

1-{[4-Carboxyl-2-(1-methylpropylcarbonylamino)phenyl}-5,5-bis-(hydroxymethyl)-pyrrolidin-2-one;

1-{[4-Carboxyl-2-(1-ethylpropyl)carbonylamino]phenyl}-5,5-bis-(hydroxymethyl)-pyrrolidin-2-one;

5-Aminomethyl-1-{[4-carboxy-2-(1-methylpropyl)carbonylamino]phenyl}-5-bis-hydroxymethylpyrrolidin-2-one; and 1-[4-Carboxyl-2-(1-ethylpropylamino)phenyl]-5-hydroxyethyl-5-hydroxymethyl-pyrrolidin-2-one;

Specific example of suitable compounds also include compound A, the ethyl ester derivative of example 8 shown below:

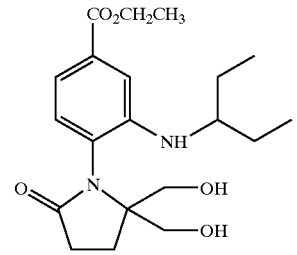

Another compound B contains an amino group in place of hydroxyl, and the structure is shown below:

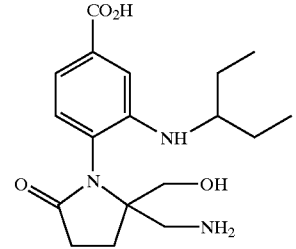

This compound was approximately twice as effective as example 8 for the inhibition of influenza neuraminidase (N2), as summarized in the Table below. This is surprising and noteworthy activity for the new compound.

Inhibition of Influenza NA

IC$_{50}$ ($\mu$M)

| Compound | Type A N2 | Type B B/Lee |
|---|---|---|
| Example 8 | 0.071 | 93 |
| Compound B | 0.040 | 49 |

Another compound is the ethyl ester derivative of Compound B, which may serve as a potential prodrug. Since Compound C is an amino acid that will be charged at all pH values, this ester derivative provides a possible prodrug form that may be more bioavailable but, once absorbed into the blood, could be acted upon by plasma or liver esterases to release the active amino acid form. The structure of Compound A is shown below:

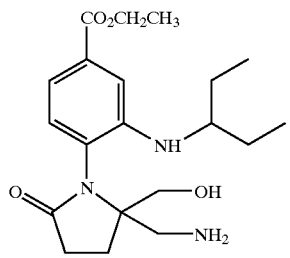

A ring-expanded homolog of example 8 is shown below as Formula (II):

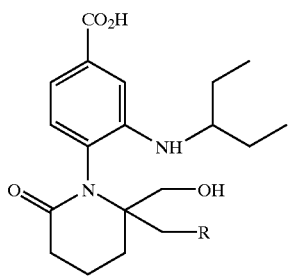

Where R=OH, $NH_2$, or guanidine.

Another compound contains a phenolic ether side chain in combination with a fourth, hydrogen bonding substituent on the benzene ring, and the structure is shown below as formula (III):

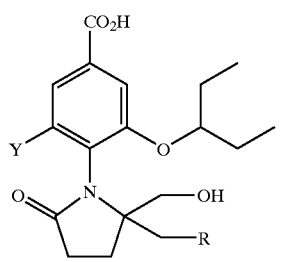

Where Y is H, OH, $NH_2$, or guanidine, and R is OH, $NH_2$, or guanidine.

An additional compound contains a benzylic alcohol or amine (or its guanidine derivative) in combination with a branched hydrophobic grouping, and the structure is illustrated below as formula (IV):

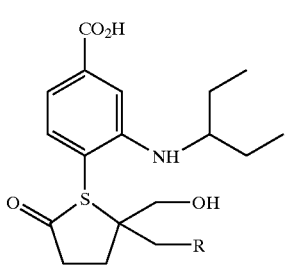

Where $R_1$=H, OH, $NH_2$, or guanidine, and $R_2$=OH, $NH_2$, or guanmdine.

Other components include a sulfur analog of example 8. The structure is shown below as formula (V):

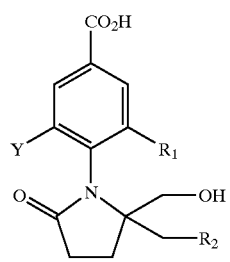

Where R is OH, $NH_2$, or guanidine.

Yet another compound include aliphatic hydrophobic groupings in combination with a fourth hydrogen bonding substituent on the benzene ring. The general structure for these components is illustrated below as formula (VI):

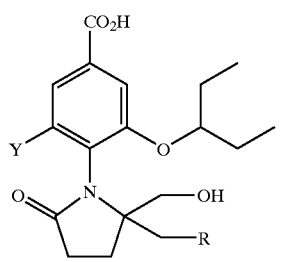

Where $R_1$ is $CH_2CH(CH_2CH_3)_2$ or $CH{=}C(CH_2CH_3)_2$, $R_2$ is OH, $NH_2$, or guanidine, and Y is H, OH, $NH_2$, or guanidine.

Finally, extra interactions can be generated between the ligand and protein binding site by extending the side chains from the pyrrolidinone ring. The structure of group of components is illustrated below as formula (VII):

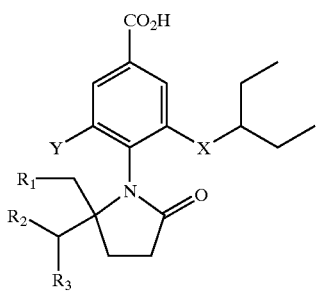

Where X is $CH_2$, O, NH, CH(OH), or $CH(NH_2)$, Y is H, OH, $NH_2$, or guanidine, $R_1$ is OH, $NH_2$, or guanidine, and R2 is H, OH, NH$_2$, or guanidine, and R$_3$ is a linear or branched alkyl group from 2–8 carbons.
The compounds of the present invention can be prepared by methods illustrated in the following schemes.
Scheme 1
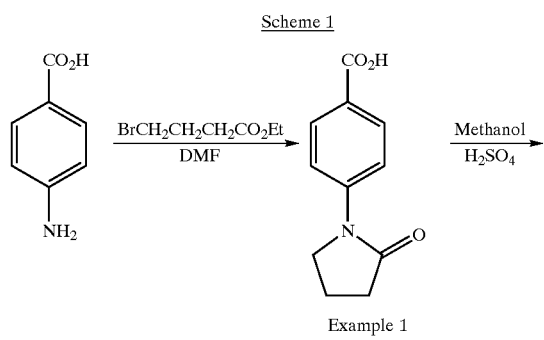
Example 1
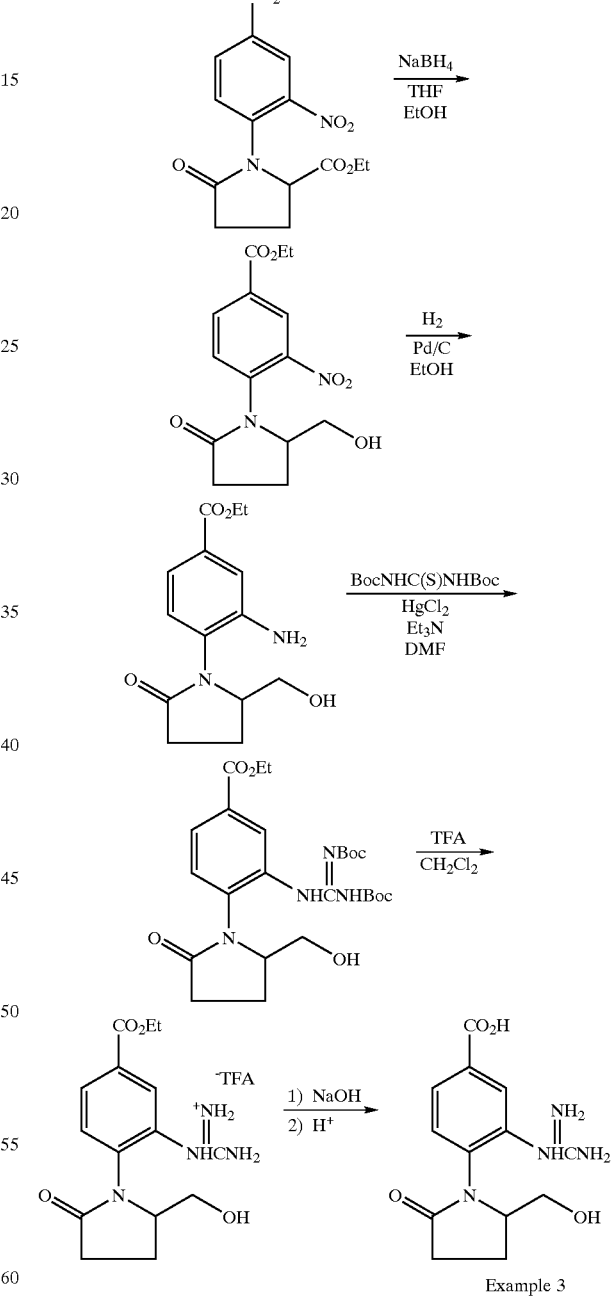
Example 3
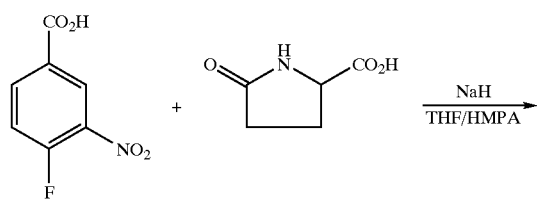
Example 2
Scheme 2

Scheme 3
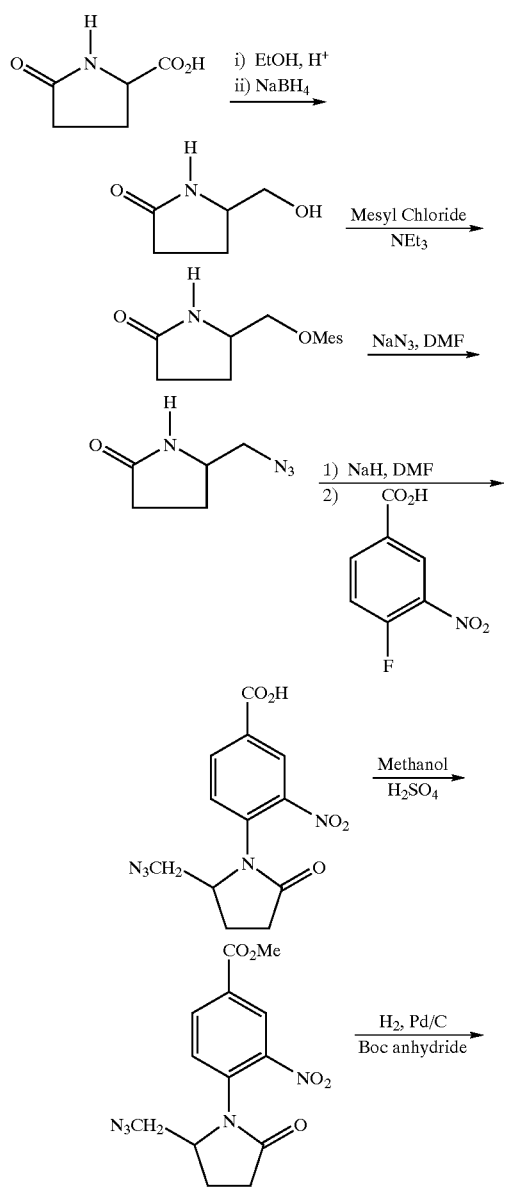
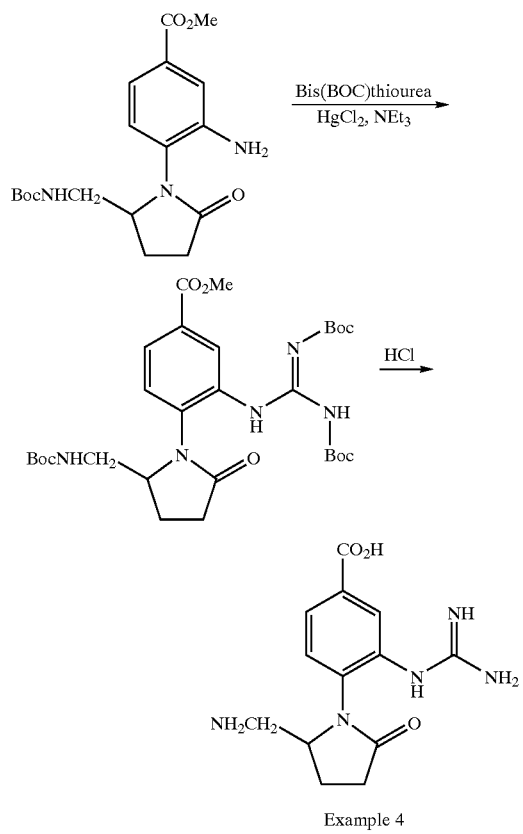
Example 4
Scheme 4
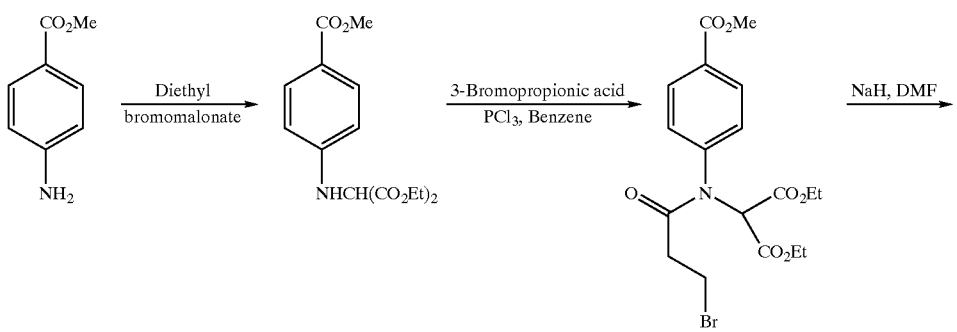

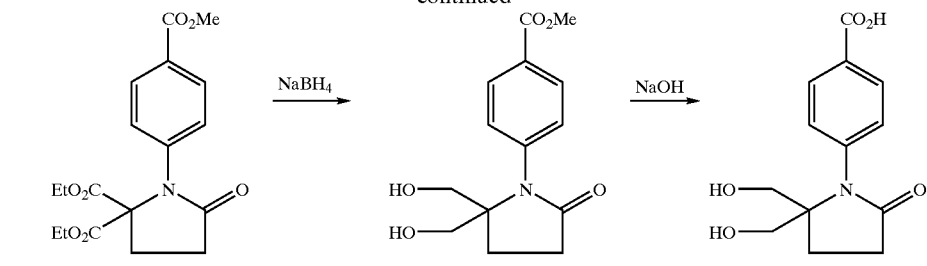
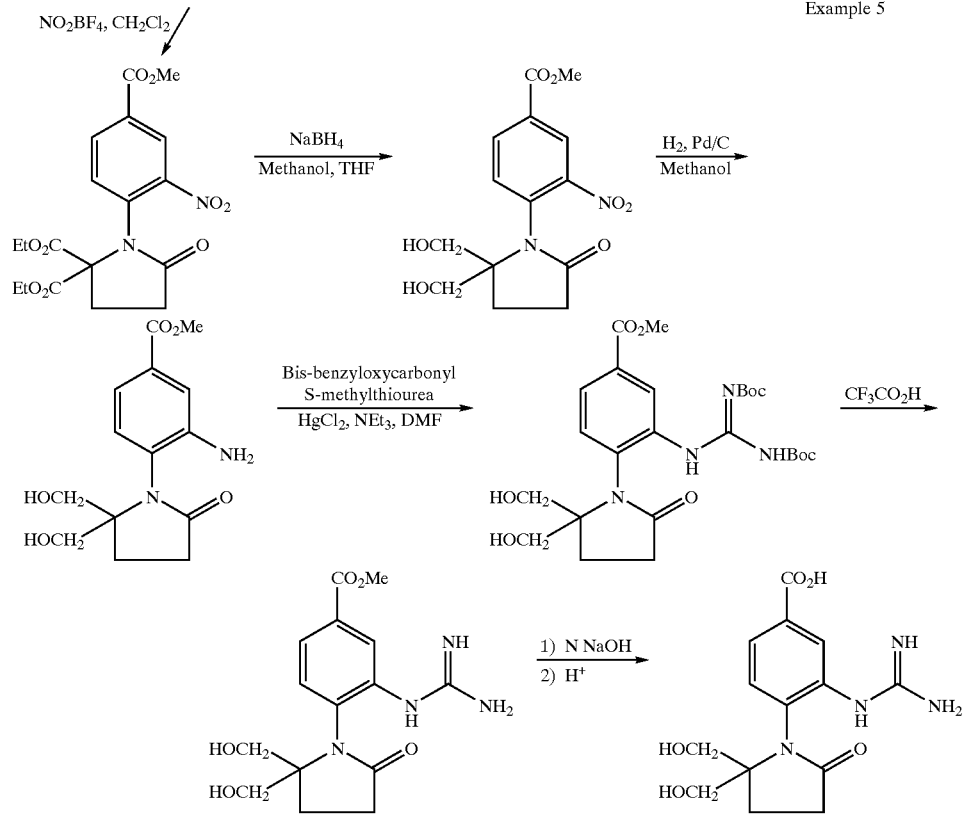
Example 6
Scheme 5
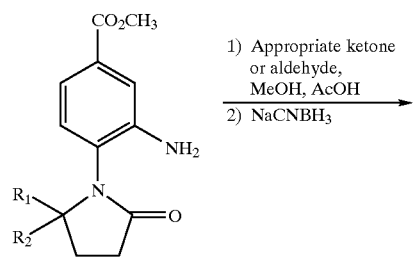
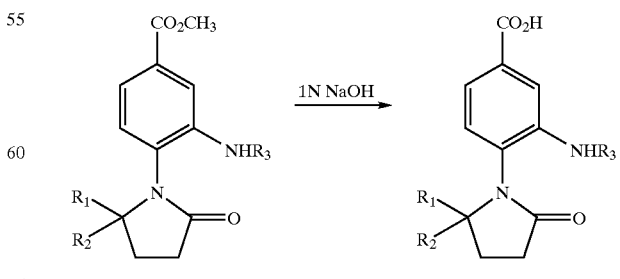
Examples 7–13

7, $R_1=R_2=H$; $R_3=CH(C_2H_5)_2$
8, $R_1=R_2=CH_2OH$; $R_3=CH(C_2H_5)_2$
9, $R_1=R_2=CH_2OH$; $R_3=CH(C_2H_5)C_3H_7$
10, $R_1=R_2=CH_2OH$; $R_3=CH(C_3H_7)_2$
11, $R_1=R_2=CH_2OH$; $R_3=CH_2CH(C_2H_5)_2$
12, $R_1=R_2=CH_2OH$; $R_3=n\text{-}C_3H_7$
10, $R_1=R_2=CH_2OH$; $R_3=n\text{-}C_5H_{11}$
14, $R_3=C_2H_5$; 15, $R_3=CH(CH_3)C_2H_5$; 16, $R_3=CH(C_2H_5)_2$
Scheme 6
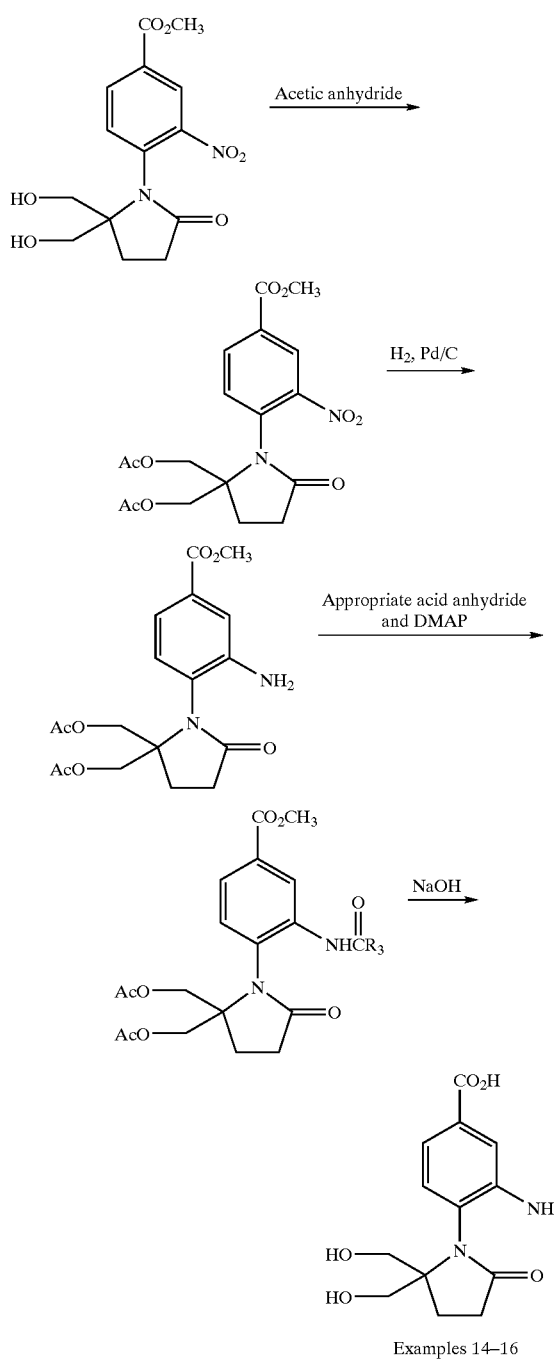
Examples 14–16
Scheme 7
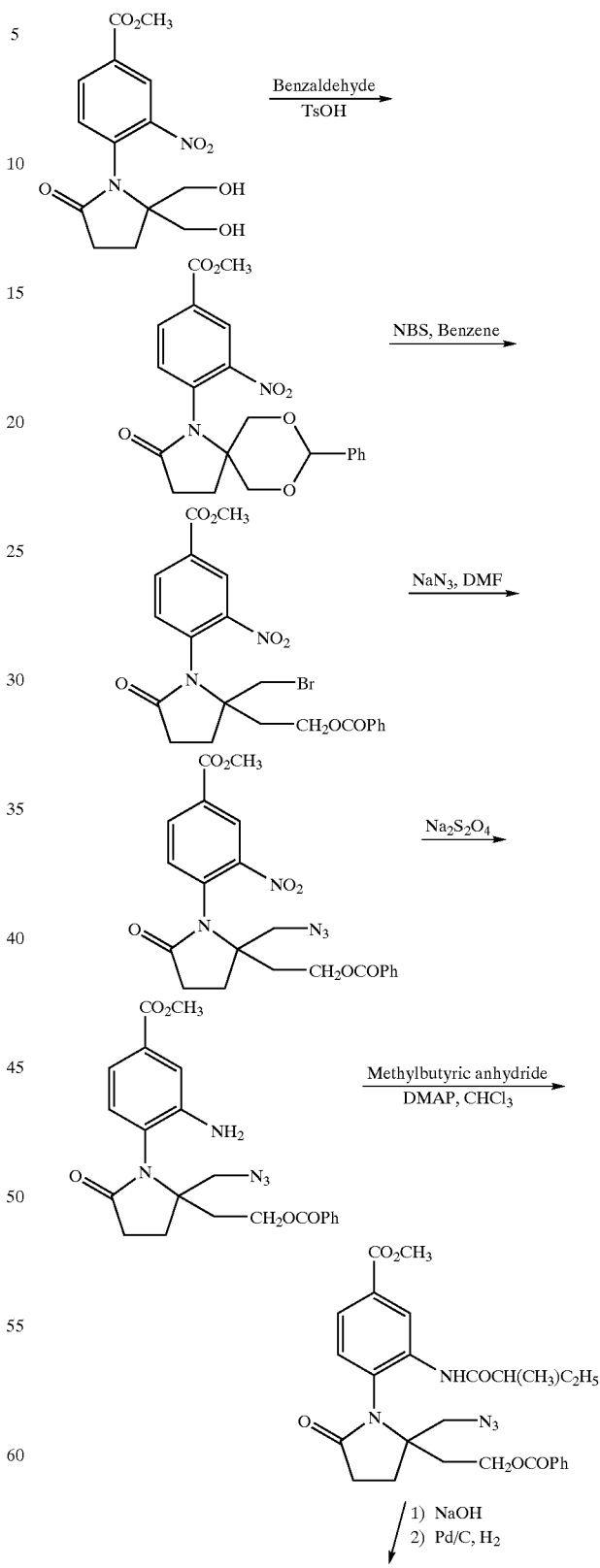

-continued

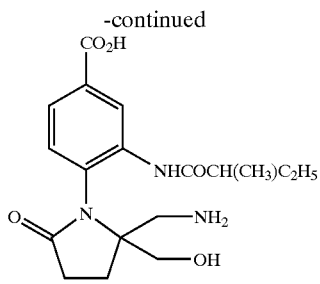

EXAMPLES

The following non-limiting examples are presented to further illustrate the present invention.

Comparison Example 1
1-(4-Carboxyphenyl)pyrrolidin-2-one

A solution of 4-aminobenzoic acid (Aldrich, 3.0 g, 21.9 mmol) and ethyl 4-bromobutyrate (Aldrich, 6.4 g, 32.8 mmol) in 20 mL of dimethylformamide was stirred at reflux for 24 h. The solvent was removed under vacuum to give a crude solid which was suspended in 15 mL of water, collected by filtration and dried. The solid was suspended in a small amount of ether (5 mL), filtered and dried to give 3.0 g (66%) of the title compound as a white solid, mp 244–246° C. (ether/ethanol), lit.mp 244–245° C. [Hopff et al. Ger. 859, 007, Sep. 22, 1952; Chem. Abstr. 52 11124h (1958)].

| Analysis: | Calcd. For $C_{11}H_{11}NO_3$: | C, 64.39; H, 5.36; N, 6.83 |
| --- | --- | --- |
| | Found: | C, 64.39; H, 5.42; N, 6.75 |

Example 2

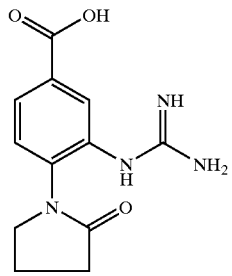

1-{2-{[(Amino) (imino)methyl]amino}4-carboxyphenyl}pyrrolidin-2-one

A mixture of 1-(4-carboxyphenyl)pyrrolidin-2-one (3.0 g, 14.6 mmol) from example 1 and sulfuric acid (0.2 mL) in 100 mL of methanol was stirred at reflux for 18 h. The solvent was removed under vacuum. The crude material was dissolved in 100 mL of ethyl acetate and the solution was washed with a saturated sodium bicarbonate solution (3×15 mL), dried and evaporated to give 3.0 g (94%) of 1-(4-methoxycarbonylphenyl)pyrrolidin-2-one as a white solid, mp 118–120° C. (chloroform/ether).

| Analysis: | Calcd. For $C_{12}H_{13}NO_3$: | C, 65.75; H, 5.94; N, 6.39 |
| --- | --- | --- |

| | Found: | C, 65.72; H, 6.00; N, 6.34 |
| --- | --- | --- |

An ice-cold mixture of the above ester (2.0 g, 9.1 mmol) in 30 mL of dichloromethane was treated with nitronium tetrafluoroborate (2.5 g, 18.8 mmol). The resulting mixture was stirred at 10° C. for 2 h and then at ambient temperature for 4 h. The reaction mixture was quenched with water (20 mL) and the organic layer was evaporated under vacuum. The white solid precipitate was collected by filtration, washed with water and dried to give 2.2 g (92%) of 1-(4-methoxycarbonyl-2-nitrophenyl)pyrrolidin-2-one, mp 159–161° C. (chloroforn/ether).

| Analysis: | Calcd. for $C_{12}H_{12}N_2O_5$: | C, 54.54; H, 4.54; N, 10.60 |
| --- | --- | --- |
| | Found: | C, 54.44; H, 4.57; N, 10.56 |

A mixture of the above nitroester (1.0 g, 3.78 mmol), and palladium on carbon (0.5 g) in 50 mL of methanol was shaken on a Parr hydrogenator for 1 h. The reaction mixture was diluted with 50 mL of methanol and the palladium on carbon was removed by filtration. The filtrate was evaporated under reduced pressure to give 0.84 g (95%) of 1-(2-amino-4-methoxycarbonylphenyl)pyrrolidin-2-one as a white solid, mp 136–138° C.

| Analysis | Calcd. for $C_{12}H_{14}N_2O_3$: | C, 61.54; H, 5.98; N, 11.96 |
| --- | --- | --- |
| | Found: | C, 61.34; H, 6.07; N, 11.82 |

An ice cold mixture of the above amine (0.09 g) in 1 mL of dry dimethylformamide was treated with 1,3-bis(tert-butoxycarbonyl)-2-methyl-2-thiopseudourea (Aldrich, 0.095 g), triethyl amine (0.116 g) and mercuric chloride (0.1 g). The resulting mixture was stirred for 4 h at 0–10° C. The solvent was evaporated under vacuum and the residue was purified by chromatography (silica gel; ether) to give 0.095 g (72%) of 1-{2-{[tert-butoxycarbonylamino)(tert-butoxycarbonylimino)methyl]amino}-4-methoxycarbonylphenyl}-pyrrolidin-2-one as an oily material which solidified upon addition of hexane. The solid was collected by filtration and dried, mp 163–164° C. (ether).

| Analysis: | Calcd. for $C_{23}H_{32}N_4O_7$: | C, 57.98; H, 6.72; N, 11.76 |
| --- | --- | --- |
| | Found: | C, 58.02; H, 6.74; N, 11.63 |

A suspension of the above ester (0.025 g, 0.05 mmol) in 1.5 mL of 1 N hydrochloric acid was stirred at reflux for 3.5 h. Solvent was removed under vacuum to give an oily material which solidified upon addition of ether to yield 0.014 g (92%) of the title compound as a white, hygroscopic solid.

| Analysis: | Calcd. for $C_{12}H_{14}N_4O_3 \cdot HCl \cdot H_2O$: | C, 45.49; H, 5.37; N, 17.69 |
| --- | --- | --- |
| | Found: | C, 45.82; H, 5.45; N, 17.99 |

Example 3

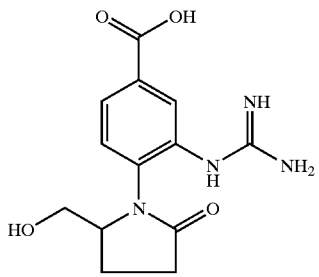

1-{-2-{[(Amino)(imino)methyl]amino}-4-carboxyphenyl}-5-hydroxymethylpyrrolidin-2-one To a suspension of a 60% sodium hydride dispersion (1.14 g, 28.4 mmol) in hexamethylphosphoramide (3 mL) was added a solution of 2-pyrrolidnone-5-carboxylic acid (Aldrich, 2.09 g, 16.2 mmol) in hexamethylphosphoramide (12 mL). The gray solution was heated to 90–95° C. for 15 min. The solution was cooled to 45° C. and then treated with 4-fluoro-3-nitrobenzoic acid (Aldrich, 1.5 g, 8.1 mmol) in hexamethylphosphoramide (8 mL). The gray-green reaction mixture was heated to 160° C., and the color gradually turned back. After 23 h the dark reaction mixture was quenched with cold 1 N hydroxhloric acid (30 mL), and extracted with ethyl acetate (60 mL). The aqueous layer was extracted with additional ethyl acetate (3×60 mL). The combined organic layers were washed with cold water (2×30 mL), saturated sodium chloride (2×30 mL) and water (2×30 mL). The extracts were dried over sodium sulfate, filtered and the solvent was removed in vacuo. The residue was purified by flash chromatography (80% ethyl acetate/hexane) on silica gel to provide 0.965 g (40%) of 1-(4-carboxy-2-nitrophenyl)-5-carboxypyrrolidin-2-one as a light-yellow solid, mp 235–237° C.

| Analysis: | Calcd. For $C_{12}H_{10}N_2O_7$: | C, 48.97; H, 3.43; N, 9.52 |
|---|---|---|
| | Found: | C, 49.21; H, 3.56; N, 9.58 |

The above diacid (0.39 g, 1.33 mmol) was dissolved in dry ethanol (4 mL), and concentrated sulfuric acid (0.2 mL). The orange reaction mixture was stirred under reflux under a nitrogen atmosphere. After 24 h the yellow reaction mixture was treated with 5% sodium bicarbonate (4 mL), and then extracted with ethyl acetate (3×10 mL). The combined extracts were dried over sodium sulfate, filtered, and the solvent was removed in vacuo to give 0.425 g (91%) of 1-(4-ethoxycarbonyl-2-nitrophenyl)-5-ethoxycarbonylpyrrolidin-2-one as a yellow oil.

| Analysis: | Calcd. for $C_{16}H_{19}N_2O_7$: | C, 54.68; H, 5.45; N, 7.98 |
|---|---|---|
| | Found: | C, 54.66; H, 5.40; N, 7.88 |

The above diester (2.0 g, 5.70 mmol) was dissolved in freshly distilled ethanol (12.5 mL) and tetrahydrofuran (12.5 mL). The orange solution was cooled to 0° C. with an ice bath, and then sodium borohydride (0.24 g, 6.27 mmol) was added in portions over a five-min period. The ice bath was removed and the temperature was allowed to equilibrate to room temperature. After 5 h the light red reaction mixture was quenched with cold 1 N hydrochloric acid (11 mL). The yellow mixture was extracted with ethyl acetate (3×45 mL). The combined organic layers were washed with saturated sodium chloride (2×45 mL), dried over sodium sulfate, filtered and the solvent was removed in vacuo. The crude mixture was purified by flash chromatography using 80% ethyl acetate/hexane to provide 0.916 g (52%) of 1-(4-ethoxycarbonyl-2-nitrophenyl)-5-hydroxymethylpyrrolidin-2-one as a yellow oil.

The above oil (0.914 g, 2.97 mmol) was dissolved in dry ethanol (114 mL), concentrated sulfuric acid (1.5 mL) and 10% palladium on carbon (0.32 g) were added and the mixture was hydrogenated at 35 psi for 1 h. The mixture was filtered through a bed of Celite®, washed with hot ethanol (20 mL), and concentrated to dryness on a rotary evaporator to give 0.745 g (95%) of a beige semi-solid, mp 90–95° C. The material was dissolved in a 5% sodium bicarbonate solution (40 mL) and sodium chloride (0.50 g) and then chloroform (40 mL) were added. The aqueous layer was separated and extracted with chloroform (2×40 mL). The combined organic layers were dried over sodium sulfate, filtered and the solvent was removed in vacuo to give 0.667 g (81%) of 1-(2-amino-4-ethoxycarbonylphenyl)-5-hydroxy-methylpyrrolidin-2-one as a white, hygroscopic solid.

The above amine (0.315 g, 1.13 mmol) was dissolved in dry dimethylformamide (12 mL), cooled to 0° C. with an ice bath and then treated with 1,3-bis(tert-butoxycarbonyl)-2-methyl-2-thiopseudourea (Aldrich, 0.493 g, 1.70 mmol), triethylamine (0.358 g, 3.50 mmol), and mercuric chloride (0.369 g, 1.36 mmol). The ice bath was removed and the reaction mixture was stirred under nitrogen at room temperature for 20 h. To the tan reaction mixture was added ethyl acetate (95 mL), and the mixture filtered through a bed of Celite®. The yellow filtrate was washed with water (50 mL), saturated sodium chloride (50 mL), and water (50 mL). The combined aqeuous layers were extracted with ethyl acetate (2×25 mL). The combined organic layers were dried over sodium sulfate, filtered, and concentrated on a rotary evaporator. The crude yellow oil was purified by flash chromatography using 80% ethyl acetate/hexane to give 0.360 g (61%) of 1-{2-{[(tert-butoxycarbonylamino)(tert-butoxycarbonylimino)-methyl]amino}-4-ethoxycarbonylphenyl}-5-hydroxymethylpyrrolidin-2-one as a foamy, yellow solid, mp 104–110° C.

The above solid (0.23 g, 0.44 mmol) was dissolved in dichloromethane (8 mL), cooled to 0° C. with an ice bath and then treated with trifluoroacetic acid (4.65 mL, 60.4 mmol). The ice bath was removed and the reaction mixture was allowed to equilibrate to ambient temperature. The reaction was stopped after 12 h. The light-red mixture was concentrated to dryness, dissolved in dichloromethane (5 mL) and again concentrated. This process was repeated three times to give 0.20 g (100%) of 1-{2-{[(amino)(imino)methyl]amino}-4-ethoxycarbonylphenyl}-5-hydroxymethylpyrrolidin-2-one as on oil.

The above oil (0. 1 9 g, 0.44 mmol) was dissolved in 1 N sodium hydroxide (5 mL) and the reaction mixture was stirred at room temperature for 2 h. To the clear mixture was added acetic acid until pH 7.5. The mixture was concentrated to half volume and cooled to give 0.06 g (47%) of the title compound as white crystals, mp 253–257° C. (water).

| Analysis: | Calcd. For $C_{12}H_{16}N_4O_4$: | C, 51.82; H, 5.69; N, 18.59 |
|---|---|---|
| | Found: | C, 51.84; H, 5.68; N, 18.42 |

Example 4

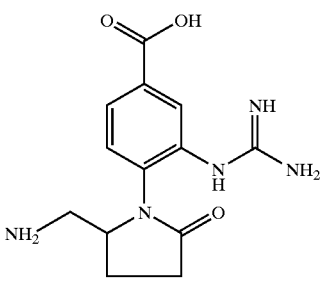

1-1-{2-{[(Amino)(imino)methyl]amino}-4-carboxyphenyl}-5-(aminomethyl)pyrrolidin-2-one An ice cold solution of 5-(hydroxymethyl)pyrrolidin-2-one (1.5 g, 13 mmol) prepared from 2-pyrrolidone-5-carboxylic acid (Valesinas et al., J. Org. Chem. 1992, 57, 2156–2160) in 20 mL of dichloromethane was treated with triethylamine (2.4 g, 23.5 mmol) and methylsulfonyl chloride (2.2 g, 19 mmol). The resulting solution was stirred at room temperature for 18 h. The reaction mixture was filtered to remove triethylamine hydrochloride and the filtrate was evaporated under reduced pressure. The crude, oily material was purified by chromatography (silica gel; 10% methanol in chloroform) to give 2.1 g of 5-(methanesulfonyloxymethyl)pyrrolidin-2-one as an oil which solidified upon addition of ether.

A mixture of the above mesylate (0.14 g, 0.72 mmol) and sodium azide (0.1 g, 1.5 mmol) in 1.5 mL of dry dimethylformamide was stirred at 80° C. for 5 h. The solvent was evaporated to dryness and the resulting residue was suspended in chloroform (25 mL), filtered and the filtrate concentrated to dryness to give an oily material which was purified by chromatography (silica gel; 10% ethanol in chloroform) to give 0.095 g (95%) of 5-azidomethylpyrrolidin-2-one as an oil.

| Analysis: | Calcd. For $C_5H_8N_4O.0.25\ H_2O$: | C, 41.52; H, 5.88; N, 38.75 |
| | Found: | C, 41.44; H, 5.94; N, 38.43 |

To a suspension of sodium hydride (0.9 g, 37.5 mmol) in 2 mL of dry dimethylformamide was added 5-azidomethylpyrrolidin-2-one (1.1 g, 7.8 mmol) in 10 mL of dimethylformamide. The resulting mixture was stirred for 15 minutes at 75° C. and cooled to ambient temperature, and a solution of 4-fluoro-3-nitrobenzoic acid (Aldrich, 1.5 g 8.1 mmol) in 8 mL of dimethylformamide was added. The reaction mixture was stirred at room temperature for 20 h. Excess sodium hydride was quenched with 2 N hydrochloric acid (2 mL). Dimethylformamide was removed under vacuum below 50° C., and the crude mixture was suspended in 10 mL of 1 N hydrochloric acid and extracted with ethyl acetate (3×50 mL). The combined organic extracts were dried and evaporated to give an oily residue which was purified by chromatography (silica gel; ether) to give 0.6 g (25%) of 5-azidomethyl-1-4(carboxy-2-nitrophenyl)pyrrolidin-2-one as a yellow solid, mp 119–121° C. (ether/ethanol).

| Anal- | Calcd. For $C_{12}H_{11}N_5O_5.0.25\ H_2O$: | C, 46.50; H, 3.71; N, 22.61 |
| ysis: | Found: | C, 46.45; H, 3.78; N, 22.72 |

A mixture of the above acid (0.52 g, 1.7 mmol) and sulfuric acid (0.1 mL) in 40 mL of methanol was stirred at reflux for 12 h. Methanol was removed under vacuum and the resulting oily material was dissolved in 100 mL of ethyl acetate. The organic layer was washed with a saturated sodium bicarbonate solution (3×10 mL). The combined extracts were dried and evaporated to give an oily material which was purified by chromatography (silica gel; ether) to give 0.52 g (96%) of 5-azidomethyl-1-(4-methoxycarbonyl-2-nitrophenyl)pyrrolidin-2-one as a colorless oil which crystallized from ether/ethanol, mp 68–70° C.

| Analysis: | Calcd. For $C_{13}H_{13}N_5O_5$: | C, 48.90; H, 4.07; N, 21.94 |
| | Found: | C, 48.81; H, 4.05; N, 22.01 |

A suspension of 10% palladium on carbon (0.21 g) in 5 mL of ethyl acetate was shaken for 5 min in the presence of hydrogen gas. The above azide (0.22 g, 0.69 mmol) and tert-butoxycarbonyl anhydride (0.155 g, 0.7 mmol) in 5 mL of ethyl acetate were added, and the resulting mixture was shaken for 2.5 h in presence of hydrogen gas. The reaction mixture was diluted with 50 mL of methanol, filtered and the filtrate concentrated to dryness under vacuum to give 0.24 g (100%) of 1-(2-amino-4-methoxycarbonylphenyl)-5-tert-butoxycarbonyl-aminomethylpyrrolidin-2-one as a colorless oil.

An ice-cold solution of the above amine (0.245 g, 0.7 mmol) in 3 mL of dry dimethylformamide under nitrogen was treated with 1,3-bis(tert-butoxycarbonyl)-2-methyl-2-thiopseudourea (0.23 g, 0.84 mmol), triethylamine (0.22 g, 2.1 mmol) and mercuric chloride (0.23 g, 0.84 mmol). The reaction mixture was then stirred at 0–10° C. for 4 h. Dimethylformamide was removed under vacuum and the crude residue was purified by chromatography (silica gel, ether) to give 0.28 g (67%) of 1-{2-{[(tert-butoxycarbonylamino)(tert-butoxycarbonylimino)methyl]amino}-4-methoxycarbonylphenyl}-5-tert-butoxycarbonylamino-methylpyrrolidin-2-one as a white solid, mp 134–136° C.

| Analysis: | Calcd. for $C_{29}H_{43}N_5O_9$: | C, 57.52; H, 7.10; N, 11.57 |
| | Found: | C, 57.49; H, 7.12; N, 11.53 |

A suspension of the above ester (0.3 g, 0.05 mmol) in 1.5 mL of 1 N hydrochloric acid was stirred at reflux for 4 h. The solvent was removed under vacuum to give 0.16 g (84%) of an oily material that was crystallized from ethanol/ether to yield the title compound as a white solid, mp 205° C. (dec).

| Analy- | Calcd. for | C, 41.50; H, 5.90; N, 17.28 |
| sis: | $C_{13}H_{19}N_5.0.5\ H_2O.0.5\ C_2H_5OH$: | |
| | Found: | C, 41.60; H, 5.74; N, 17.24 |

Example 5

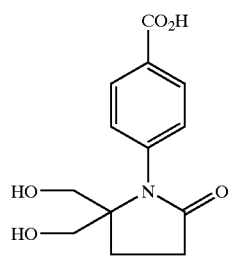

1-(4-Carboxyphenyl)-5,5-bis-(hydroxymethyl)pyrrolidin-2-one

A mixture of methyl 4-aminobenzoate (3.1 g, 20.5 mmol) and diethyl bromomalonate (2.45 g, 10.2 mmol) in a round bottom flask was placed in an oven at 115° C. for 16 h. The reaction mixture, which had turned into a solid cake, was suspended in 20 mL of benzene and filtered. The filtrate was diluted with 50 mL of benzene and the organic layer was washed with 2 N hydrochloric acid (3×10 mL), water (10 mL), dried ($Na_2SO_4$) and evaporated to give an oily material which solidified upon standing. The crude was recrystallized from ether/hexane to give 2.7 g (85%) of diethyl (4-methoxycarbonylphenyl)aminomalonate, mp 66–69° C. (ether/hexane).

Analysis: Calcd. For $C_{15}H_{19}NO_6$: C, 56.52; H, 4.35; N, 10.15; Found: C, 56.55; H, 4.40; N, 10.13

A mixture of the above ester (1.1 g, 3.5 mmol), 3-bromopropionic acid (1.1 g, 7.2 mmol) and phosphorus trichloride (1 mL) in 12 mL of benzene was stirred at reflux for 30 h. The reaction mixture was diluted with 50 mL of benzene and the organic layer was washed with a saturated sodium bicarbonate solution (3×15 mL), water (10 mL), 1 N hydrochloric acid (10 mL) and water (10 mL). The organic layer was dried and concentrated to give 1.4 g (89%) of diethyl N,N-[(2-bromoethylcarbonyl)(4-methoxycarbonylphenyl)amino]malonate as an oily residue.

A suspension of sodium hydride (60% in oil) (0.07 g, 2.9 mmol) in 10 mL of dry dimethylformamide was treated with the above bromo compound (0.517, 1.1 mmol) in 7 mL of dimethylformamide. The reaction mixture was stirred at room temperature for 2 h. Excess sodium hydride was quenched with 1 mL of 1 N hydrochloric acid. Solvent was removed under vacuum and the resulting crude, oily residue was suspended in 50 mL of ethyl acetate and the mixture was washed with water (3×10 mL). The organic layer was dried and concentrated to give 0.415 g (98%) of 5,5-bis-ethoxycarbonyl-1-(4-methoxycarbonylphenyl)pyrrolidin-2-one as an oil.

| Analysis: | Calcd. For $C_{18}H_{21}NO_7$: | C, 59.50; H,5.78; N, 3.85 |
|---|---|---|
| | Found: | C, 58.95; H, 5.77; N, 3.78 |

To an ice-cold solution of the above ester (0.5 g, 1.37 mmol) in 1.5 mL of tetrahydrofuran and 1.5 mL of methanol was added sodium borohydride (0.2 g, 5.2 mmol) in small portions over a period of 20–25 min. The reaction mixture was then stirred at 0° C. for 4 h. An additional portion of sodium cyanoborohydride (0.1 g, 2.6 mmol) was added and stirring was continued for 5 h at 0–5° C. The reaction mixture was quenched with 5 mL of 0.5 N hydrochloric acid. The organic solvent was evaporated and the residue was extracted with ethyl acetate (5×25 mL). The combined extracts were dried and concentrated to give 0.4 g of oil. This oil was purified by chromatography (silica gel; 10% ethanol in ether) to yield 0.15 g (39%) of 5,5-bis-(hydroxymethyl)-1-(4-methoxycarbonylphenyl)pyrrolidin-2-one.

A solution of the above ester (0.06 g, 0.21 mmol) in 2 mL of 1 N sodium hydroxide was stirred at room temperature for 3.5 h. The pH of the reaction mixture was adjusted to 2 with 1 N hydrochloric acid and the mixture was extracted with ethyl acetate (5×10 mL). The combined extracts were dried and concentrated to give 0.04 g (70%) of residue. The solid was suspended in ether and collected by filtration to give the title compound, mp 195–197° C.

| Analysis: | Calcd. For $C_{13}H_{15}NO_5$: | C, 58.86; H, 5.66; N, 5.28 |
|---|---|---|
| | Found: | C, 58.40; H, 5.78; N, 4.92 |

Example 6

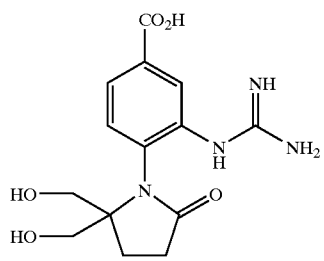

1-{2-{[(Amino)(imino)methyl]amino}-4-carboxyphenyl}-5,5-bis-(hydroxymethyl)-pyrrolidin-2-one

An ice-cold solution of 5,5-bis-ethoxycarbonyl-1-(4-methoxycarbonylphenyl)-pyrrolidin-2-one (0.45 g, 1.23 mmol) from Example 5 in 5 mL of dichloromethane was treated with nitronium tetrafluoroborate (0.55 g, 4.1 mmol). The resulting mixture was stirred at 5–10° C. for 3 h. The reaction mixture was evaporated to dryness and the residue was dissolved in 50 mL of ethyl acetate. The organic layer was washed with water (3×15 mL), dried and concentrated to give 0.44 g (95%) of 5,5-bis-ethoxycarbonyl-1-(4-methoxy-carbonyl-2-nitrophenyl)pyrrolidin-2-one as an oil which solidified upon standing, mp 81–82° C. (ether).

| Analysis: | Calcd. For $C_{18}H_{20}N_2O_9$: | C, 52.94; H, 4.9; N, 6.86 |
|---|---|---|
| | Found: | C, 52.91; H, 4.89; N, 6.9 |

An ice-cold solution of the above nitro compound (4.1 g, 10.0 mmol) in a mixture of 50 mL of tetrahydrofuran and 50 mL of methanol was treated with small portions of sodium borohydride (1.8 g, 47 mmol) over a period of 1 h. Stirring was continued for 4 h after which time additional sodium borohydride (0.5 g, 13 mmol) was added. After an additional 4 h of stirring, sodium borohydride (0.5 g, 13 mmol) was again added and the stirring continued for 6 h at 0° C. The reaction mixture was then quenched with 1 N hydrochloric acid (25 mL). The reaction mixture was concentrated to about 30 mL and the product was extracted with ethyl acetate (3×50 mL). The combined organic layers were dried and concentrated to give an oily residue which was purified by chromatography (silica gel; 10% ethanol in ether) to give 2 g (62%) of 5,5-bis-hydroxymethyl-4-(4methoxycarbonyl-2-nitrophenyl)pyrrolidin-2-one, mp 144–145° C.

| Analysis: | Calcd. For $C_{14}H_{16}N_2O_7$: | C, 51.85; H, 4.94; N, 8.64 |
| --- | --- | --- |
| | Found: | C, 51.95; H, 4.97; N, 8.66 |

A suspension of the above alcohol (0.8 g, 2.5 mmol) in 25 mL of methanol was treated with 10% palladium on carbon (0.5 g) and the resulting mixture was shaken in the presence of hydrogen gas for 1 h. The reaction mixture was diluted with 50 mL of methanol, filtered and concentrated to dryness under vacuum to give an oily material which solidified upon addition of ether to give 0.63 g (87%) of 1-(2-amino-4-methoxycarbonylphenyl)-5,5-bis-(hydroxymethyl)pyrrolidin-2-one, mp 192–194° C.

| Analysis: | Calcd. For $C_{14}H_{18}N_2O_5 \cdot 0.25\ CH_3OH$: | C, 56.60; H, 6.29; N, 9.27 |
| --- | --- | --- |
| | Found: | C, 56.51; H, 6.28; N, 9.24 |

An ice-cold solution of the above amine (0.254 g, 0.86 mmol) in 3 mL of dry dimethylformamide was treated with bis-benzyloxycarbonyl-S-methythiourea (Aldrich, 0.425 g, 1.2 mmol), mercuric chloride (0.33 g, 1.2 mmol) and triethylamine (0.25 g, 2.4 mmol). The resulting mixture was stirred at 0° C. for 3 h and then allowed to warm to ambient temperature and stirred for 12 h. The solvent was removed under vacuum and the crude residue was purified by chromatography (silica gel; ether) to give 0.37 g (71%) of 5,5-bis-(hydroxymethyl)-1-{4-methoxycarbonyl-2-{[(phenylmethoxycarbonylamino)(phenyl-metboxycarbonylimino)methyl]-amino}phenyl}pyrrolidin-2-one as a colorless oil.

A solution of the above oil (0.35 g, 0.57 mmol) in 1 mL of methanol was treated with 1 N sodium hydroxide (2.5 mL), and the resulting suspension was stirred at ambient temperature for 16 h. The pH of the reaction mixture was adjusted to 3 with 1 N hydrochloric acid, and the mixture was purified by ion exchange column (Dowex; 1.4 N ammonium hydroxide) to give 0.1 1 g (59%) of the title compound as an ammonium salt, MS (ES) 323.

Example 7

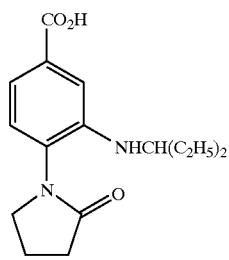

1-[4-Carboxy-2-(3-pentylamino)phenyl]pyrrolidin-2-one

A solution of 1-(2-amino-4-methoxycarbonylphenyl)pyrrolidin-2-one (0.5 g, 2.1 mmol) from example 2, 3-pentanone (0.19 g, 2.2 mmol) and triethylamine (0.44 g, 4.3 mmol) in 10 mL of dry dichloromethane was treated with 1 m solution of titanium tetrachloride (3.5 mL, 3.5 mmol) in dichloromethane. The resulting mixture was stirred at ambient temperature for 18 h after which time sodium cyanoborohydride (0.41 g, 6.5 mmol) was added. Stirring was continued for an addition 3 h. The reaction mixture was quenched with 1 N sodium hydroxide (2 mL) and the organic layer was separated and concentrated under vacuum. The residue was extracted with ethyl acetate (3×30 mL) and the combined extracts were dried and concentrated to give an oil which was purified by column chromatography (silica gel; 10% ethanol in ether) to yield 0.16 g (25%) of 1-[4-methoxycarbonyl-2-(3-pentylamino)phenyl]pyrrolidin-2-one.

| Analysis: | Calcd. for $C_{17}H_{24}N_2O_3 \cdot 0.75\ H_2O$: | C, 64.25; H, 7.56; N, 8.81 |
| --- | --- | --- |
| | Found: | C, 64.43; H, 7.67; N, 8.79 |

A solution of the above ester (0.150 g, 0.49 mmol) in 1 mL of methanol was treated with 1N sodium hydroxide (2 mL) and the resulting mixture was stirred at ambient temperature for 16 h. The reaction mixture was acidified with glacial acetic acid and a solid precipitated. The solid was collected by filtration, washed with water and dried to give 0.125 g (87%) of the title compound, mp 178–180° C.

| Analysis: | Calcd. For $C_{16}H_{22}N_2O_3 \cdot 0.5\ H_2O$: | C, 64.21; H, 7.69; N, 9.36 |
| --- | --- | --- |
| | Found: | C, 64.35; H, 7.38; N, 9.39 |

Example 8

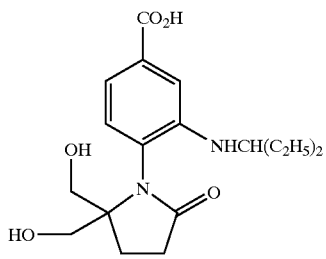

1-[4-Carboxy-2-(3-pentylamino)phenyl]-5,5-bis-(hydroxymethyl)pyrrolidin-2-one

A solution of 1-(2-amino-4-methoxycarbonylphenyl)-5,5-bis-hydroxymethylpyrrolidin-2-one (0.1 g, 0.34 mmol) from Example 6 in 1 mL of dichloromethane and 0.5 mL of acetic acid was treated with 3-pentanone (0.2 g, 2.3 mmol) and sodium cyanoborohydride (0.075 g, 1.2 mmol). The resulting mixture was stirred at ambient temperature for 6 h after which time additional 3-pentanone (0.2 g, 2.3 mmol), sodium cyanoborohydride (0.075 g, 1.2 mmol) and methanol (0.5 mL) were added and stirring continued for 12 h. A third portion of 3-pentanone (0.3. g, 3.4 mmol) and sodium cyanoborohydride (0.15 g, 2.3 mmol) was added and the stirring continued for an additional 16 h. The reaction mixture was quenched with 10 mL of a saturated sodium bicarbonate solution, and the mixture was extracted with ethyl acetate (3×50 mL). The combined organic extracts were dried and concentrated. The residue was purified by chromatography (silica gel; 5% ethanol in ether) to give 0.105 g (82%) of 1-[4-methoxycarbonyl-2-(3-pentylamino)phenyl]-5,5-bis-(hydroxymethyl)pyrrolidin-2-one as a white solid, mp 183–185° C.

| Analysis: | Calcd. For $C_{19}H_{28}N_2O_5$: | C, 62.63; H, 7.69; N, 7.69 |
| --- | --- | --- |
| | Found: | C, 62.69; H, 7.79; N, 7.69 |

A suspension of the above ester (0.07 g, 0.19 mmol) in 1 N sodium hydroxide (1 mL) was stirred at ambient temperature for 12 h. Upon acidification of the reaction mixture with glacial acetic acid, a solid precipitated. This solid was collected by filtration and dried to give 0.05 g (75%) of the title compound as a white solid, mp 220–221° C.

| Analysis: | Calcd. For $C_{18}H_{26}N_2O_5$: | C, 61.71; H, 7.43; N, 8.00 |
| --- | --- | --- |
| | Found: | C, 61.46; H, 7.50; N, 7.92 |

Example 9

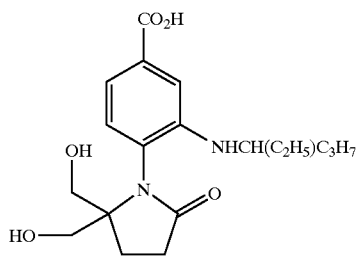

1-[4-Carboxy-2-(3-hexylamino)phenyl]-5,5-bis-(hydroxymethyl)pyrrolidin-2-one

A solution of 1-(2-amino-4-methoxycarbonylphenyl)-5,5-bis-(hydroxymethyl)pyrrolidin-2-one (0.15 g, 0.51 mmol) from Example 6 in 1 mL of dichloromethane and 0.5 mL of acetic acid was treated with 3-hexanone (0.3 g, 3 mmol) and sodium cyanoborohydride (0.1 g, 1.6 mmol). The resulting mixture was stirred at ambient temperature for 6 h after which time additional 3-hexanone (0.1 g, 1 mmol), sodium cyanoborohydride (0.05 g, 0.8 mmol) and methanol (0.5 mL) were added. Stirring was continued for 12 h. A third portion of 3-hexanone (0.17 g, 1.7 mmol) and sodium cyanoborohydride (0.055 g, 0.9 mmol) was added and stirring continued for an additional 16 h. The reaction mixture was quenched with 10 mL of a saturated sodium bicarbonate solution and extracted with ethyl acetate (3×50 mL). The combined extracts were dried and concentrated. The residue was purified by chromatography (silica gel; 5% ethanol in ether) to give 0.175 g (90%) of 1-[2-(3-hexylamino)-4-methoxycarbonylphenyl]-5,5-bis-(hydroxymethyl)pyrrolidin-2-one as an oil.

A suspension of the above oil (0.15 g, 0.4 mmol) in 1 N sodium hydroxide (2 mL) and methanol (1 mL) was stirred at ambient temperature for 12 h. Upon acidification of the reaction mixture with glacial acetic acid, a solid precipitated. The solid was collected by filtration and dried to give 0.125 g (86%) of the title compound as a white solid, mp 232–233° C.

| Analysis: | Calcd. For $C_{19}H_{28}N_2O_5$: | C, 62.64; H, 7.69; N, 7.69 |
| --- | --- | --- |
| | Found: | C, 62.46; H, 7.73; N, 7.58 |

Example 10

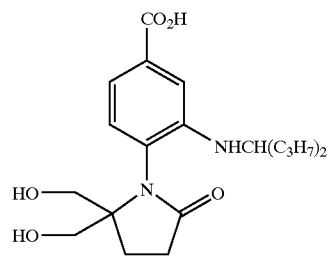

1-[4-Carboxy-2-(4-heptylamino)phenyl]-5,5-bis-(hydroxymethyl)pyrrolidin-2-one

A solution of 1-(2-amino-4-methoxycarbonylphenyl)-5,5-bis-(hydroxymethyl)pyrrolidin-2-one (0.15 g, 0.51 mmol) from Example 6 in 1 mL of dichloromethane and 0.3 mL of acetic acid was treated with 4-heptanone (0.175 g, 1.53 mmol) and sodium cyanoborohydride (0.05 g, 0.8 mmol). The resulting mixture was stirred at ambient temperature for 12 h after which time addition 4-heptanone (0.175 g, 1.53 mmol), sodium cyanoborohydride (0.05 g, 0.8 mmol) and acetic acid (0.3 mL) were added. Stirring was continued for 12 h. The reaction mixture was quenched with 10 mL of a saturated sodium bicarbonate solution and the mixture was extracted with ethyl acetic (3×50 mL). The combined extracts were dried and concentrated. The residue was purified by chromatography (silica gel; 5% ethanol in ether) to give 0.15 g (75%) of 1-[2-(4-heptylamino)-4-methoxycarbonylphenyl]-5,5-bis-(hydroxymethyl) pyrrolidin-2-one as a white solid, mp 139–140° C.

| Analysis: | Calcd. For $C_{21}H_{32}N_2O_5$: | C, 64.28; H, 8.16; N, 7.14 |
| --- | --- | --- |
| | Found: | C, 64.44; H, 8.14; N, 7.17 |

A suspension of the above ester (0.08 g, 0.2 mmol) in 1 N sodium hydroxide (1.5 mL) and methanol (1 mL) was stirred at ambient tmperature for 12 h. Upon acidification of the reaction mixture with glacial acetic acid, a solid precipitated. The solid was collected by filtration and dried to give 0.07 g (90%) of the title compound, mp 227–229° C.

| Analysis | Calcd. For $C_{20}H_{30}N_2O_5$: | C, 63.49; H, 7.93; N, 7.40 |
| --- | --- | --- |
| | Found: | C, 63.21; H, 7.99; N, 7.18 |

Example 11

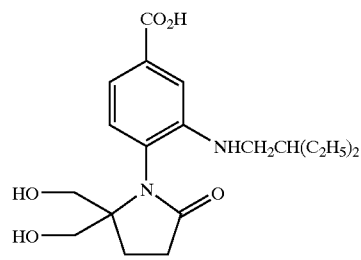

1-{4-Carboxy-2-[3-pentyl)methylaminolphenyl}-5,5-bis-(hydroxymethyl)pyrrolidin-2-one.

A suspension of 1-(2-amino-4-methoxycarbonylphenyl)-5,5-bis-(hydroxymethyl)pyrrolidin-2-one (0.1 g, 0.34 mmol) from Example 6 in 2 mL of dichloromethane was treated with acetic acid (0.1 g, 1.6 mmol), 2-ethylbutyraldehyde (0.065 g, 0.65 mmol) and sodium cyanoborohydride (0.035 g, 0.55 mmol). The resulting mixture was stirred at ambient temperature for 2 h. The reaction mixture was quenched with a saturated sodium bicarbonate solution (2 mL) and the mixture was extracted with ethyl acetate (3×25 mL). The combined organic layers were dried and concentrated to give 0.14 g of crude oil which was purified by chromatography (silica gel; 10% ethanol in ether) to yield 0.115 g (90%) of 5,5-bis-(hydroxymethyl)-1-{4-methoxycarbonyl-2-[(3-pentyl)methylamino]phenyl}pyrrolidin-2-one as white solid, mp 142–143° C.

| Analysis: | Calcd. For $C_{20}H_{30}N_2O_5$: | C, 63.49; H, 7.93; N, 7.40 |
|---|---|---|
| | Found: | C, 63.53; H, 7.92; N. 7.39 |

A solution of the above ester (0.1 g, 0.26 mmol) in 0.5 mL of methanol and 2 mL of 2 N sodium hydroxide was stirred at ambient temperature for 6 h. The reaction mixture was acidified with glacial acetic acid. Volatile solvents were removed under vacuum, the aqueous residue was diluted with 2 mL of water and cooled during which time a solid precipitated. The solid was collected by filtration, washed with water and dried to give 0.08 g (84%) of the title compound, mp 169–171° C.

| Analysis: | Calcd. For $C_{19}H_{28}N_2O_5 \cdot 0.25\ H_2O$: | C, 61.87; H, 7.73; N, 7.59 |
|---|---|---|
| | Found: | C, 61.51; H, 7.65; N, 7.35 |

Example 12

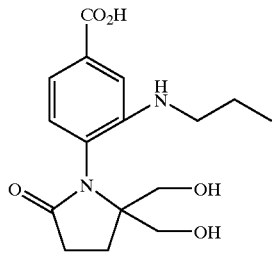

1-[4-Carboxy-2-(propylaminolphenyl]-5,5-bis(hydroxymethyl)pyrrolidin-2-one

A suspension of 1-(2-amino-4-methoxycarbonylphenyl)-5,5-bis(hydroxymethyl)-pyrrolidin-2-one (160 mg, 0.54 mmol) from example 6 in dichloromethane (1.0 mL) and acetic acid (0.1 mL) was treated with propionaldehyde (80 mg, 1.37 mmol) and NaCNBH$_3$ (52 mg, 0.83 mmol). The resulting mixture was stirred at room temperature for 1 h. The resulting mixture was quenched with NaHCO$_3$ solution (2 mL) and the product was extracted into ethyl acetate (5×10 mL). The combined organic layers were dried (Na$_2$SO$_4$), filtered and concentrated to give an oil which was purified by flash chromatography (silica gel; 10% ethanol in ether) to give 170 mg (93.0%) of 1-[4-methoxycarboxy-2-(propylamino]phenyl]-5,5-bis(hydroxymethyl)pyrrolidin-2-one as an oil which crystallized upon addition of ether, mp 119–120° C.

| Analysis: | Calcd. For $C_7H_{24}N_2O_5$: | C, 60.71; H, 7.14; N, 8.33 |
|---|---|---|
| | Found: | C, 60.59; H, 7.18; N, 8.37 |

A solution of the above ester (140 mg, 0.41 mmol) in methanol (1 mL) and 1 N NaOH (1 mL) was stirred at room temperature for 3 h. Acidification of the reaction mixture with glacial acetic acid followed by evaporation of methanol at 40° C., resulted in white precipitate, which was collected by filtration and dried to give 120 mg (90%) of the title compound, mp 180–181° C.

| Analysis: | Calcd. For $C_{16}H_{22}N_2O_5$: | C, 59.62; H, 6.83; N, 8.69 |
|---|---|---|
| | Found: | C, 59.59; H, 6.88; N, 8.60 |

Example 13

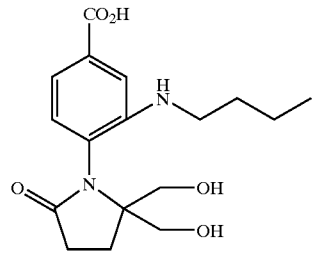

1-[4-Carboxy-2-(pentylaminolphenyl]-5,5-bis(hydroxymethyl)pyrrolidin-2-one

A suspension of 1-(2-amino-4-methoxycarbonylphenyl)-5,5-bis(hydroxymethyl)-pyrrolidin-2-one (170 mg, 0.57 mmol) from example 6 in dichloromethane (1.0 mL) and acetic acid (0.1 mL) was treated with valeradehyde (125 mg, 1.45 mmol) and NaCNBH$^3$ (55 mg, 0.87 mmol). The resulting mixture was stirred at room temperature for 1 h. The resulting mixture was quenched with NaHCO$_3$ solution (2 mL) and the product was extracted into ethyl acetate (5×10 mL). The combined organic layers were dried (Na$_2$SO$_4$), filtered and concentrated to give an oil which was purified by flash chromatography (silica gel; 10% ethanol in ether) to give 200 mg (95.0%) of 1-[4-methoxycarboxy-2-(pentylamino]phenyl]-5,5-bis(hydroxymethyl)pyrrolidin-2-one as an oil which crystallized upon addition of ether, mp 148–149° C.

| Analysis: | Calcd. For $C_{19}H_{28}N_2O_5 \cdot 0.25H_2O$ | C, 61.87; H, 7.73; N, 7.59 |
|---|---|---|
| | Found: | C, 62.06; H, 7.77; N, 7.56 |

A solution of the above ester (150 mg, 0.41 mmol) in methanol (1 mL) and 1 N NaOH (1 mL) was stirred at room temperature for 4 h. Acidification of the reaction mixture with glacial acetic acid followed by evaporation of methanol at 40° C., resulted in a white precipitate, which was collected by filtration, washed with water and dried to give 135 mg (94%) of the title compound, mp 176–177° C.

| Analysis: | Calcd. For $C_{18}H_{26}N_2O_5$: | C, 61.71; H, 7.42; N, 8.00 |
| --- | --- | --- |
| | Found: | C, 61.63; H, 7.51; N, 7.92 |

Example 14

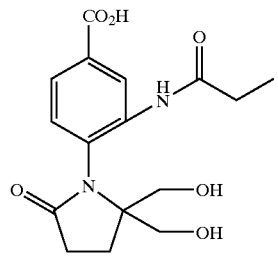

1-[4-Carboxy-2-(ethylcarbonylamino)phenyl]-5,5-bis(hydroxymethyl)pyrrolidin-2-one A suspension of 1-[4-methoxycarbonyl-2-(nitro)phenyl]-5,5-bis(hydroxymethyl)-pyrrolidin-2-one (500 mg, 1.54 mmol) from example 6 in acetic anhydride (0.5 mL) was treated with DMAP (15 mg) and the resulting mixture was stirred at room temperature for 1.5 h. The reaction mixture was dried under high vacuum and the resulting crude oil was purified by flash chromatography (silica gel; 10% ethanol in ether) to give 620 mg (98.5%) of 1-[4-methoxycarbonyl-2-(nitro)phenyl]-5,5-bis(acetyloxymethyl)pyrrolidin-2-one as an oil which solidified upon standing, mp, 61–63° C.

| Analysis: | Calcd. for $C_{18}H_{20}N_2O_9$: | C,52.94;H,4.90;N,6.86 |
| --- | --- | --- |
| | Found: | C,53.09;H,4.99;N,6.76 |

A solution of the above nitro compound (620 mg, 1.52 mmol) and 10%Pd/C (100 mg) in methanol (20 mL) was shaken in presence of hydrogen gas at 30 psi for 1 h. The reaction mixture was diluted with methanol (50 mL), filtered and the filtrate concentrated to give 520 mg (91%) of 1-[4-methoxycarbonyl-2-(amino)phenyl]-5,5-bis(acetyloxy-methylpyrrolidin-2-one as white solid, mp 158–160° C.

A mixture of the above amine (150 mg, 0.4 mmol), propionic anhydride (0.5 mL) and DMAP (15 mg) in chloroform (1 mL) was stirred at room temperature for 4 h. The reaction mixture was dried under high vacuum below 40° C. and the resulting crude oil was purified by flash chromatography on silica gel (10% ethanol in ether) to give 165 mg (96.0%)) of 1-[4-methoxycarboxy-2-(ethylcarbonylamino)phenyl]-5,5-bis(acetyloxymethyl) pyrrolidin-2-one as an oil which solidified upon rapid stirring in ether, mp 124–125° C.

| Analysis: | Calcd. for $C_{21}H_{26}N_2O_8$: | C, 58.06; H, 5.99; N, 6.45 |
| --- | --- | --- |
| | Found: | C, 57.91; H, 6.10; N, 6.25 |

A solution of the above ester (154 mg, 0.35 mmol) in methanol (1 mL) and 1N NaOH (2 mL) was stirred for 12 h. The reaction mixture was quenched with 1 N HCl and methanol was removed under vacuum. The resulting precipitate was filtered, washed with water and dried to give 100 mg (86.0%) of the title compound, mp 217–218° C.

| Analysis: | Calcd. For $C_{16}H_{20}N_2O_6$: | C, 57.14; H,5.95; N, 8.33 |
| --- | --- | --- |
| | Found: | C, 56.94; H, 6.07; N, 8.21 |

Example 15

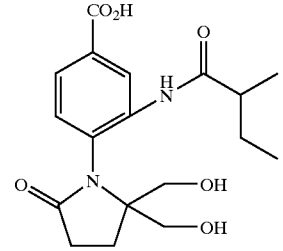

1-{[4-Carboxy-2-(1-methylpropyl)carbonylamino]pheny}-5,5-bis(hydroxymethyl)-pyrrolidin-2-one A mixture of 1-[4-methoxycarbonyl-2-(amino)phenyl]5,5-bis(acetyloxymethyl-pyrrolidin-2-one (250 mg, 0.66 mmol) from example 14, methylbutyric anhydride (2.0 mL) and DMAP (dimethylaminopyridine) (25 mg) in chloroform (3 mL) was stirred at reflux temperature for 12 h. The reaction mixture was dried under high vacuum below 40° C. and the resulting crude oil was purified by flash chromatography on silica gel (10% ethanol in ether) to give 200 mg (66.0%) of 1-{[4-methoxycarbonyl-2-(1-methylpropyl)carbonylamino]phenyl}-5,5-bis(acetyloxym ethyl)pyrrolidin-2-one as an oil which was crystallized from ether, mp 125–126° C.

| Analysis: | Calcd. for $C_{23}H_3ON_2O_8$: | C, 59.74; H, 6.49; N, 6.06 |
| --- | --- | --- |
| | Found: | C, 59.78; H, 6.50; N, 6.09 |

A solution of the above ester (150 mg, 0.32 mmol) in methanol (0.5 mL) and 1N NaOH (2 mL) was stirred for 12 h. The reaction mixture was quenched with 1N HCl and methanol was removed under vacuum. The resulting precipitate was filtered, washed with water and dried to give 105 mg (89.0%) of the title compound, mp 254–255° C.

| Analysis: | Calcd. for $C_{18}H_{24}N_2O_6$: | C, 59.34; H, 6.59; N, 7.69 |
| --- | --- | --- |
| | Found: | C, 59.25; H, 6.60; N, 7.66 |

Example 16

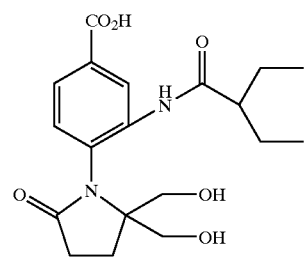

1-{[4-Carboxy-2-(1-ethylpropyl)carbonylaminol phenyl]-5,5-bis(hydroxymethyl)-pyrrolidin-2-one A mixture of 1-[4-methoxycarbonyl-2-(amino)phenyl]-5,5-bis(acetyloxymethyl-pyrrolidin-2-one (250 mg, 0.66 mmol) from example 14, ethylbutyric anhydride (2.0 mL) and DMAP (25 mg) in chloroform (3 mL) was stirred at reflux temperature for 18 h. The reaction mixture was dried under high vacuum below 40° C. and the resulting crude oil was purified by flash chromatography on silica gel (10% ethanol in ether) to give 180 mg (51.0%) of 1-{[4-methoxycarbonyl-2-(1-ethylpropy)carbonylamino]phenyl}-5,5-bis(acetyloxymethyl)pyrrolidin-2-one as an oil.

A solution of the above ester (120 mg, 0.23 mmol) in methanol (0.5 mL) and 1N NaOH (1.5 mL) was stirred for 14 h. The reaction mixture was quenched with 1N HCl and methanol was removed under vacuum. The resulting precipitate was filtered, washed with water and dried to give 80 mg (94.0%) of the title compound, mp 234–235° C.

| Analysis: | Calcd. for $C_{19}H_{26}N_2O_6$: | C, 60.31; H, 6.88; N, 7.40 |
|---|---|---|
| | Found: | C, 60.15; H, 6.95; N, 7.28 |

Example 17

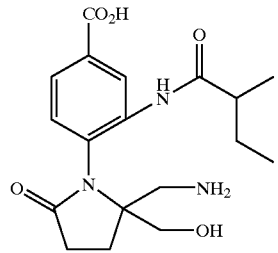

5-Aminomethyl-1-{[4-carboxy-2-(1-methylpropyl)carbonylamino]phenyl}-5-hydroxymethylpyrrolidin-2-one A suspension of 1-[4-methoxycarbonyl-2-(nitro)phenyl]-5,5-bis(hydroxymethyl)-pyrrolidin-2-one (1.8 g, 5.55 mmol) from example 6, benzaldehyde (2.0 g, 18.86 mmol) and p-toluenesulphonic acid (50 mg) in dry toluene (50 mL) was stirred at reflux temperature for 24 h, while collecting the generated water with a Dean-stark trap. The reaction mixture was concentrated to dryness and the resulting oil was dissolved in ethyl acetate (100 mL) and washed with saturated NaHCO$_3$ (3×15 mL), dried (sodium sulfate), filtered and concentrated. The resulting semisolid was suspended in ether (10 mL), cooled and the solid collected by filtration to give 1.4 g of the product. The mother liquor was evaporated to dryness to give an oil which was purified by flash chromatography (silica gel; 5% ethanol in ether) to give an additional 700 mg (91%) of 1-[4-methoxycarbonyl-2-(nitro)phenyl]-5,5-[bis(hydroxymethyl)benzylidene acetal]-pyrrolidin-2-one, mp 155–156° C. (I crop) & 203–204° C. (from chromatography). From 1H nmr it appears that both compounds are isomers. The mixture of both compounds was taken for further reactions.

| Analysis: | Calcd. for $C_{21}H_{20}N_2O_7$: | C, 61.16; H, 4.85; N, 6.80 |
|---|---|---|
| | Found: | C, 61.12; H, 4.90; N, 6.81 |

A solution of benzylidene acetal (1.4 g, 3.40 mmol) and freshly dried bromosuccinimide (0.8 g, 4.5 mmol) in freshly dried benzene (77 mL) was stirred at room temperature for 18 h under nitrogen atmosphere. The reaction mixture was concentrated to dryness below 40° C. and the resulting crude solid was dissolved in chloroform (70 mL), washed with water (3×15 mL), dried (sodium sulfate), filtered and concentrated to give an off white solid. This was suspended in methanol (5 mL) and the solid was collected by filtration and dried to give 1.5 g (93%) of 5-bromomethyl-1-[4-methoxycarbonyl-2-(nitro)phenyl]-5-phenylcarbonyloxymethylpyr rolidin-2-one, mp 183–184° C.

| Analysis: | Calcd. for $C_{21}H_{19}N_2O_7Br$: | C, 51.43; H, 3.88; N, 5.71 |
|---|---|---|
| | Found: | C, 51.49; H, 3.83; N, 5.57 |

A mixture of the above bromo compound (1.1 g, 2.24 mmol) and anhydrous NaN$_3$ (0.70 g, 10.7 mmol) in anhydrous DMF (9 mL) was stirred at 90° C. for 28 h under nitrogen atmosphere. The reaction mixture was diluted with ethyl acetate (100 mL), washed with water (3×10 mL), dried (sodium sulfate), filtered and the filtrate concentrated to give a solid. The solid was suspended in ether, filtered and dried to give 700 mg (69.0%) of 5-azidomethyl-1-[4-methoxycarbonyl-2-(nitro)phenyl}-5-phenylcarbonyloxymethylpyrrolidin-2-one, mp 214–215° C.

| Analysis: | Calcd. for $C_{21}H_{19}N_5O_7 \cdot 0.5H_2O$: | C, 54.54; H, 4.11; N, 15.15 |
|---|---|---|
| | Found: | C, 54.85; H, 4.29; N, 14.84 |

A suspension of the above nitro compound (650 mg, 1.43 mmol) in THF (15 mL) and H$_2$O (5 mL) was treated with Na$_2$S$_2$O$_4$ (0.70 g, 4.02 mmol). The resulting mixture was stirred at room temperature for 1 h and at 50–55° C. for 5 min. The reaction mixture became homogenous during this time. The reaction mixture was then stirred at room temperature for 5 h. The reaction mixture was concentrated to dryness under high vacuum and the resulting solid was triturated with ethyl acetate (3×25 mL), filtered and the filtrate concentrated to give 560 mg (92%) of 5-azidomethyl-1-[4-methoxycarbonyl-2-(amino)phenyl]-5-phenylcarbonyloxymethylpyrrolidin-2-one.

| Analysis: | Calcd. for $C_{21}H_{21}N_5O_5$ | C, 59.57; H, 4.96; N, 16.55 |
|---|---|---|
| | Found | C, 59.21; H, 4.72; N, 16.10 |

A mixture of the above amine (150 mg, 0.35 mmol), DMAP (50 mg) and methylbutyric anhydride (1.0 mL) in chloroform (2 mL) was stirred at reflux temperature for 12 h. The reaction mixture was concentrated to dryness under high vacuum and the resulting oil was purified by flash chromatography (silica gel; 1% ethanol in ether) to give 150 mg (92%) of 5-azidomethyl-1-{[4-methoxycarbonyl-2-(1-methylpropyl)-carbonylamino]phenyl]-5-phenylcarbonyloxymethy)pyrrolidin-2-one as an oil.

A suspension of the above ester (150 mg, 0.30 mmol) in methanol (1 mL) and 1 N NaOH (2 mL) was stirred at room temperature for 16 h. The mixture was neutralized with 1N HCl The resulting solid was collected by filtration, washed with water and dried to give 100 mg (87.0%) of 5-azidomethyl-1-{[4-methoxycarbonyl-2-(1-methylpropyl)carbonylamino]-5-hydroxymethylpyrrolidin-2-one A suspension of the above azide (50 mg, 0.130 mmol) and 10% Pd/C (50 mg) in methanol (5 mL) was shaken in the presence of hydrogen gas at 30 psi for 1.5 h. The reaction mixture was diluted with methanol (25 mL), filtered and the filtrate concentrated to give 45 mg (98%) of the title compound as a very hygroscopic glassy solid.

| Anal- | Calcd. for $C_{18}H_{25}N_3O_5 \cdot C_2H_5OH$: | C, 58.68; H, 7.51; N, 10.27 |
|---|---|---|
| ysis: | Found: | C, 58.57; H, 6.95; N, 9.75 |

Example 18

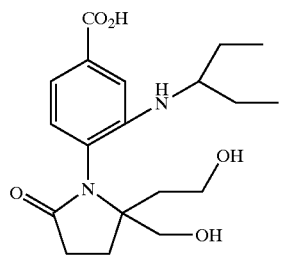

1-[4-Carboxy-2-(1-ethylpropylamino)phenyl]-5-hydroxyethyl-5-hydroxymethyl-pyrrolidin-2-one To a suspension of 60% NaH (0.52 g, 13.0 mmol) in dry DMF (12 mL) was added diethyl (4-methoxycarbonylphenyl)aminomlonate (4.0 g, 12.9 mmol). The resulting mixture was stirred at room temperature for 15 min. and bromoethyl acetate (2.4 g, 14.3 mmol) was added to it. The mixture was stirred further for 36 h at room temperature. The reaction was quenched with 1N HCl (10 mL) and the product was extracted into ethyl acetate (3×50 mL). The combined organic extracts were washed with $H_2O$ (25 mL), dried (sodium sulfate), filtered and the filtrate concentrated to give an oil which was purified by flash chromatography (silica gel, 2:1 ether/hexane) to give an oil which was crystallized from ether to give 4.1 g (80.0%) of diethyl (acetyloxyethyl) (4-methoxycarbonylphenyl)aminomlonate as white crystals, mp 88–89° C.

| Analysis: | Calcd. for $C_{19}H_{25}NO_8$ | C, 57.71; H, 6.37; N, 3.54 |
|---|---|---|
| | Found: | C, 57.64; H, 6.30; N, 3.51 |

An ice-cold suspension of the above malonate (1.0 g, 2.53 mmol) in dry methanol (12 mL) was treated with Na (250 mg, 10.9 mmol). The mixture was stirred for 1 h at 0° C. and then quenched with 1N HCl (10 mL). Methanol was removed under vacuum and the product was extracted into ethyl acetate (3×25 mL), dried (sodium sulfate) and filtered. The filtrate was concentrated to give an oil which was purified by flash chromatography (silica gel, ether) to give 0.5 g (84.0%) of 3-(4-methoxycarbonylphenylamino)-γ-butyrolactone as white solid, mp 136–138° C.

A solution of the above lactone (50 mg, 0.213 mmol) in dry THF (1 mL) cooled to −78° C. was treated with lithium diisopropylamide (28 mg, 0.26 mmol). After 20 min of stirring, ethylacrylate (32 mg, 0.32 mmol) was added and the stirring continued for 4 h between −70 to −60° C. The reaction mixture was quenched with 1N HCl (1 mL) and the product was extracted into ethyl acetate (3×15 mL). The combined extracts were dried (sodium sulfate), filtered and the filtrate concentrated to an oil which was purified by flash chromatography (silica gel, 6.4% ethanol in ether) to give 36 mg (55.3%) of spiro 3-(γ-butyrolactone)-5-[N-(4-methoxycarbonylphenyl)pyrrolidin-2-one] (36 mg, 55.3%) as a white solid, mp 102–104° C.

| Analysis: | Calcd. for C15H15NO5: | C, 62.27; H, 5.28; N, 4.84 |
|---|---|---|
| | Found: | C, 62.29; H, 5.25; N, 4.77 |

An ice-cold solution of the above Spiro compound (80 mg, 0.28 mmol) in methylene chloride (2 mL) was treated with nitronium tetrafluoroborate (188 mg, 1.42 mmol). The reaction mixture was stirred at 0° C. for 6 h and at room temperature for 10 h. The reaction mixture was quenched with $H_2O$ (2 mL) and $CH_2Cl_2$ was removed under vacuum. The aqueous layer was extracted with ethyl acetate (5×15 mL). The combined extracts were washed with brine (5 mL), dried (sodium sulfate), filtered and the filtrate concentrated to give a yellow solid. This was purified by flash chromatography (silica gel, 5% ethanol in ether) to give 76 mg (81.0%) of spiro 3-(γ-butyrolactone)-5-[N-(4-methoxycarbonyl-2-nitrophenyl)pyrrolidin-2-one] as a white solid, mp 147–150° C.

| Analysis: | Calcd. for $C_{15}H_{14}N_2O_5$: | C, 53.89; H, 4.22; N, 8.37 |
|---|---|---|
| | Found: | C, 53.49; H, 4.26; N, 8.23 |

An ice-cold solution of the above nitro spiro lactone (35 mg, 0.10 mmol) in a mixture of dry methanol (0.5 mL) and dry THF (0.5 ml) was treated with $NaBH_4$ (19 mg, 0.5 mmol) in small portions over a period of 25–30 min. The reaction mixture was further stirred at 0–5° C. for 4 h and quenched with 1N HCl (0.75 mL). The solvent was removed under vacuum and the aqueous layer was extracted with ethyl acetate (4×15 mL) The combined extracts were dried (sodium sulfate), filtered and the filtrate concentrated to give a semisolid which was purified by flash chromatography (silica gel, 6.4% ethanol in ether) to give 28 mg (79%) of 1-[4-methoxycarbonyl-2-(nitro)phenyl]-5-hydroxyethyl-5-hydroxymethylpyrrolidin-2-one, as yellow crystals, mp 151–153° C.

| Analysis: | Calcd. For $C_{15}H_{18}N_2O_7$: | C, 53.24; H, 5.36; N, 8.28 |
|---|---|---|
| | Found: | C, 53.14; H, 5.44; N, 8.22 |

A mixture of the above nitro compound (50 mg, 0.15 mmol) and 10% Pd/C (47 mg) in methanol (10 mL) was shaken in the presence of hydrogen gas at 30 psi for 1 h. The reaction mixture was diluted with methanol (10 mL), filtered and the filtrate concentrated to dryness to give 44 mg (99%) of 1-[4-methoxycarbonyl-2-(amino)phenyl]-5-hydroxyethyl-5-hydroxymthylpyrrolidin-2-one as an oil.

A solution of the above amine (90 mg, 0.29 mmol) in dichloroethane (1 mL) and acetic acid (0.5 mL) was treated with 3-pentanone (182 mg, 2.01 mmol) and $NaCNBH_3$ (68 mg). The resulting mixture was stirred at room temperature for 18 h. To this mixture were further added 3-pentanone (182 mg, 2.01 mmol) and $NaCNBH_3$ (68 mg, 1.08 mmol) and the stirring continued for an additional 17 h. The reaction was quenched with saturated sodium bicarbonate and the product was extracted into ethyl acetate (5×20 mL). The combined organic extracts were dried (sodium sulfate), filtered and the filtrate concentrated to give an oil which was purified by flash chromatography (silica gel, 8% ethanol in ether) to give 78 mg (71.0%) of 1-(4-methoxycarbonyl-2-(1-ethylpropylamino) phenyl]-5-hydroxyethyl-5-hydroxymethylpyrrolidin-2-one as a white solid, mp 141–143° C.

A suspension of the above ester (60 mg, 0.16 mmol) in 1N NaOH (1 mL) was stirred at room temperature for 17 h. The reaction mixture was neutralized with acetic acid and evaporated to dryness on high vacuum. The resulting solid was dissolved in $H_2O$ (3 mL) and extracted with ethyl acetate (7×5 mL). The combined organic layers were dried (sodium sulfate), filtered and the filtrate concentrated to give a semisolid which was suspended in ether and filtered to give 40 mg (69.0%) of the title compound as yellow crystals, mp 188–190° C.

Biochemistry

The in vitro assay is based on the method reported by von Itzstein et al. (EP Application 92309634.6). The neuraminidase from the H1N9 strain of influenza was obtained by the method described by Laver et al. (Virology 1984, 137, p. 314–323) Values for the $IC_{50}$ were measured via a spectrofluorometric technique that uses the fluorogenic substrate 2'-(4-methylumbelliferyl)-α-D-acetylneuramic acid. This substrate is cleaved by neuraminidase to yield a fluorescent product that can be quantified. The assay mixture contains inhibitors at various concentrations (four to six points) and enzyme in 32.5 mM MES [(2-(N-morpholino) ethanesulfonic acid] buffer, 4 mM $CaCl_2$ at pH=6.5 (total volume=80 µL). The reaction is started by the addition of 20 µL of the substrate to a final concentration of 75 µM. After 10 min at 37° C., 2.4 mL of 0.1 M glycine/NaOH (pH=10.2) is added to 0.1 mL of the reaction mixture to terminate the reaction. A blank is run with the same substrate solution with no enzyme. Fluorescence is read using an Aminco-Bowman fluorescence spectrophotometer (excitation: 360 nm and emission: 450 nm) and substrate blanks were subtracted from the readings. The $IC_{50}$ is calculated by plotting percent inhibition versus the inhibitor concentration, and determination of each point is performed in duplicate.

| | Neuraminidase Inhibition Activity ($IC_{50}$ in µM | |
|---|---|---|
| Example | NR | N2 |
| 1 | >7000 | |
| 2 | 250 | |
| 3 | 22 | |
| 4 | 2600 | |
| 5 | 700 | |
| 6 | 5 | |
| 7 | 220 | |
| 8 | 0.048 | |
| 9 | 116 | |
| 10 | 5.5 | 8.1 |
| 11 | — | 3.5 |
| 12 | — | 15.5 |
| 13 | — | 36.4 |
| 14 | — | 1.5 |
| 15 | — | 0.18 |
| 16 | — | 0.82 |
| 17 | — | 6.0 |
| 18 | — | 184 |

The above results illustrate the significant neuraminidase inhibiting activity achievable by compounds of the present invention. Example 8 is orally bioavailable.

Crystallography

Complexes between neuraminidase and inhibitor molecules were prepared by transferring HIN9 neuraminidase crystals into 2 mL of the phosphate buffer solution in which the inhibitor has been dissolved. The concentration of the inhibitor compound was adjusted to be 2 mM. The crystal was allowed to equilibrate in the buffer solution for about one day and then removed from the solution and mounted in a glass capillary for X-ray diffraction data collection. All X-ray intensity measurements were recorded with a Siemens X-100 multiwire area detector on a Rigaku RU-300 rotating anode generator operating at 100 mA and 50 kV and a copper anode. The crystal to detector distance was 160 mm and the detector was offset to collect 2.4 Å data. Intensity data were measured on 0.1° oscillation frames at 240 s of exposure per frame. Each crystal yielded 600–700 frames of data before radiation damage to the crystals prevented further data collection.

The intensity data were processed using the XENGEN package of programs. The integrated intensities were scaled and merged to produce a final data set containing only unique reflections. The final data sets were complete to 2.5 Å resolution. All refinement was carried out using the program XPLOR. The starting model for refinement was the 2.0 Å refined native N9 structure. Difference Fourier maps to 2.5 Å were calculated using the calculated phases from the refined model. Analysis of the electron density maps was performed on a Silicon Graphics Indigo Extreme 2 computer graphics workstation using the graphics program QUANTA. Idealized models for the inhibitor molecules were manually fitted to the difference electron density. These inhibitor models were later included in the XPLOR refinement.

Dosage and Formulation

The antiviral compounds of this invention can be administered as prophylaxis or treatment for viral infections by any means that produces contact of the active agent's site of action with the viral neuraminidase in the body of a human, mammal, bird, or other animal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms, the kind of concurrent treatment; the frequency of treatment; and the effect desired. A daily dosage of active ingredient can be expected to be about 0.001 to 1000 milligram (mg) per kilogram (kg) of body weight, with the preferred dose being 0.1 to about 50 mg/kg.

Dosage forms (compositions suitable for administration) contain from about 1 mg to about 100 mg of active ingredient per unit. In these pharmaceutical compositions, the active ingredient will ordinarily be present in an amount of about 0.5–95 % by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms. The active ingredient can also be administered intranasally (nose drops) or by inhalation. Other dosage forms are potentially possible such as administration transdermally, via a patch mechanism or ointment.

Gelatin capsules contain the active ingredient and powdered carriers, such as lactose, starch, cellulose derivatives, magnesium stearate, stearic acid, and the like.

Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere or enteric coated for selective disintegration in the gastrointestinal tract.

Liquid dosage forms for oral administration can contain coloring flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and, if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in Remington's Pharmaceutical Sciences, Mack Publishing Company, a standard reference text in this field.

Useful pharmaceutical dosage forms for administration of the compounds according to the present invention can be illustrated as follows:

Capsules

A large number of unit capsules are prepared by filling standard two-piece hard gelatin capsules each with 100 mg of powdered active ingredient, 150 mg of lactose, 50 mg of cellulose, and 6 mg of magnesium stearate.

Soft Gelatin Capsules

A mixture of active ingredient in a digestible oil such as soybean oil, cottonseed oil, or olive oil is prepared and injected by means of a positive displacement pump into gelatin to form soft gelatin capsules containing 100 mg of the active ingredient. The capsules are washed and dried.

Tablets

A large number of tablets are prepared by conventional procedures so that the dosage unit was 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate coatings may be applied to increase palatability or delay absorption.

Moreover, the compounds of the present invention can be administered in the form of nose drops or a nasal inhaler.

Various modifications of the invention in addition to those shown and described herein will be apparent to those skilled in the art from the foregoing description. Such modifications are also intended to fall within the scope of the appended claims.

The foregoing disclosure includes all the information deemed essential to enable those skilled in the art to practice the claimed invention. Because the cited applications may provide further useful information, these cited materials are hereby incorporated by reference in their entirety.

The foregoing description of the invention illustrates and describes the present invention. Additionally, the disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. The embodiments described hereinabove are further intended to explain best modes known to practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed is:

1. A compound having the formula:

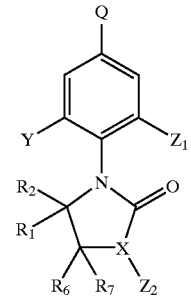

wherein

Q is $CO_2H$, $SO_3H$, $PO_3H_2$, $NO_2$ or esters thereof;

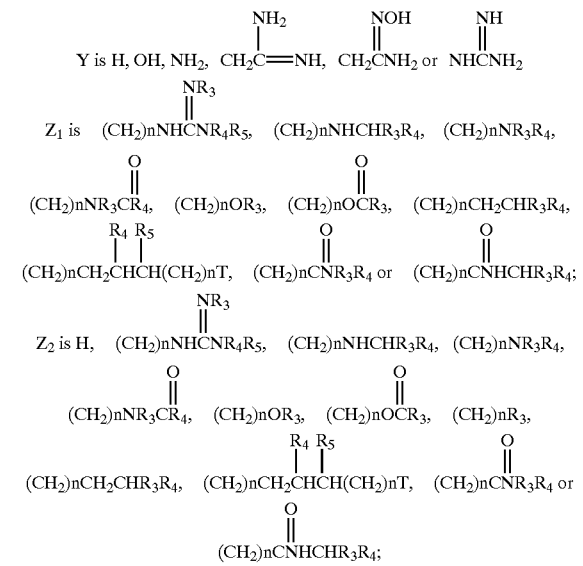

T is H, OH or $OH_2$
n is 0–3;
X is $(CH_2)_n$;
each of $R_1$ and $R_2$ individually is H, $(CH_2)mA$, or $(CH_2)mZ_2$, and $R_1$ and $R_2$ can be the same or different;
each of $R_6$ and $R_7$ individually is H, $(CH_2)mA$, or $(CH)mZ_2$, and $R_6$ and $R_7$ can be the same or different;

m is 1–3,

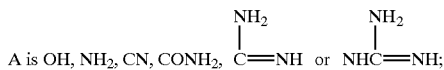

A is OH, NH$_2$, CN, CONH$_2$, C(NH$_2$)=NH or NHC(NH$_2$)=NH;

each of R$_3$, R$_4$, R$_5$ individually is H, lower alkyl, branched alkyl, cycloalkyl, aryl or alkaryl, and R$_3$, R$_4$ and R$_5$ can be the same as or can differ from each other; and pharmaceutically acceptable salts thereof.

2. The compound of claim 1 being 1-{2-{[(Amino)(imino)methyl]amino}-4-carboxyphenyl}pyrrolidin-2-one.

3. The compound of claim 1 being 1-{2-{[(Amino)(imino)methyl]amino}-4-carboxyphenyl}-5-(hydroxymethyl)pyrrolidin-2-one.

4. The compound of claim 1 being 1-{2-{[(Amino)(imino)methyl]amino}-4-carboxyphenyl}-5-(aminomethyl)pyrrolidin-2-one.

5. The compound of claim 1 being 1-(4-Carboxyphenyl)-5,5-bis-(hydroxymethyl)pyrrolidin-2-one.

6. The compound of claim 1 being 1-{2-{[(Amino)(imino)methyl]amino}-4-carboxyphenyl}-5,5-bis-(hydroxymethyl)pyrrolidin-2-one.

7. The compound of claim 1 being 1-{4-Carboxy-2-(3-pentylamino)phenyl}pyrrolidin-2-one.

8. The compound of claim 1 being 1-[4-Carboxy-2-(3-pentylamino)phenyl]-5,5-bis-(hydroxymethyl)pyrrolidin-2-one.

9. The compound of claim 1 being 1-[4-Carboxy-2-(3-hydroxylamino)phenyl]-5,5-bis-(hydroxymethyl)pyrrolidin-2-one.

10. The compound of claim 1 being 1-[4-Carboxy-2-(4-heptylamino)phenyl]-5,5-bis-(hydroxymethyl)pyrrolidin-2-one.

11. The compound of claim 1 being 1-{4-Carboxy-2-[(3-pentyl)methylamino]phenyl}-5,5-bis-(hydroxymethyl)pyrrolidin-2-one.

12. The compound of claim 1 being 1-[4-Carboxy-2-(propylamino)phenyl]-5,5-bis-(hydroxymethyl)pyrrolidin-2-one.

13. The compound of claim 1 being 1-[4-Carboxy-2-(pentylamino)phenyl]-5,5-bis-(hydroxymethyl)pyrrolidin-2-one.

14. The compound of claim 1 being 1-[4-Carboxy-2-(ethylcarbonylamino)phenyl]-5,5-bis-(hydroxymethyl)pyrrolidin-2-one.

15. The compound of claim 1 being 1-{[4-Carboxy-2-(1-methylpropyl)carbonylamino]phenyl}-5,5-bis-(hydroxymethyl)pyrrolidin-2-one.

16. The compound of claim 1 being 1-{[4-Carboxy-2-(1-ethylpropyl)carbonylamino]phenyl}-5,5-bis-(hydroxymethyl)pyrrolidin-2-one.

17. The compound of claim 1 being 5-Aminomethyl-1-{[4-Carboxy-2-(1-methylpropyl)carbonylamino]phenyl}-5-hydroxymethylpyrrolidin-2-one.

18. The compound of claim 1 being 1-[4-Carboxy-2-(1-ethylpropylamino)phenyl]-5-hydroxyethyl-5-hydroxymethyl-pyrrolidin-2-one.

19. The composition for inhibiting influenza virus neuraminidase, comprising a pharmaceutically acceptable carrier and an amount effect for inhibiting influenza virus neuraminidase of a compound according to claim 1.

20. A method for inhibiting influenza virus neuraminidase, comprising the step of: administering to a patient in need thereof a composition comprising a pharmaceutically acceptable carrier and an amount effective for inhibiting influenza virus neuramindase of a compound according to claim 1.

21. A method of treating influenza virus infection, comprising the step of administering to a patient in need thereof a composition comprising a pharmaceutically acceptable carrier and an amount effective for inhibiting influenza virus neuraminidase of a compound according to claim 1.

22. The compound according to claim 1, wherein Q is CO$_2$H or an ester thereof.

23. The compound according to claim 22, wherein Q is a lower alkyl ester.

24. The compound according to claim 22, wherein Q is CO$_2$CH$_2$CH$_3$.

25. The compound according to claim 22 wherein at least one of R$_1$ and R$_2$ is CH$_2$OH.

26. The compound according to claim 22 wherein at least one of R$_1$ and R$_2$ is CH$_2$NH$_2$.

27. The compound according to claim 22 wherein R$_1$ is CH$_2$OH and R$_2$ is CH$_2$NH$_2$.

28. The compound according to claim 27 wherein Z is (CH$_2$)$_n$NHCHR$_3$R$_4$ wherein each of R$_3$ and R$_4$ is a lower alkyl group.

29. The compound according to claim 28 wherein n is 0, and R$_3$ and R$_4$ are both ethyl groups.

30. The compound according to claim 1 wherein at least one of R$_1$ and R$_2$ is CH$_2$OH.

31. The compound according to claim 30 wherein R$_1$ is CH$_2$OH and R$_2$ is CH$_2$NH$_2$.

32. The compound according to claim 1 wherein at least one of R$_1$ and R$_2$ is CH$_2$NH$_2$.

33. The compound according to claim 1 wherein Z is (CH$_2$)$_n$NHCHR$_3$R$_4$ wherein each of R$_3$ and R$_4$ is a lower alkyl.

34. The compound according to claim 33 wherein n is 0 and R$_3$ and R$_4$ are both ethyl groups.

35. A compound having the formula:

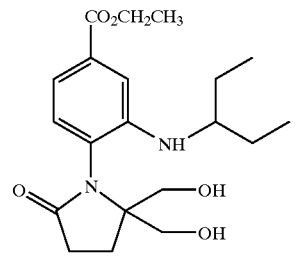

36. A compound having the formula:

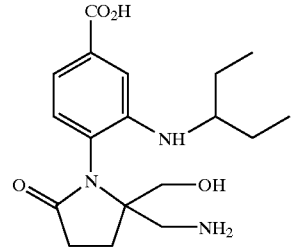

37. A compound having the formula

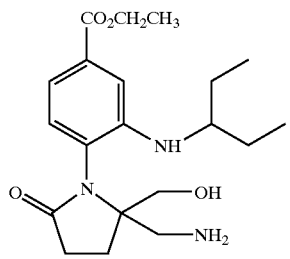

38. A compound having the formula

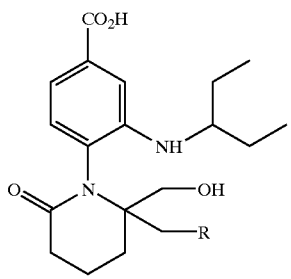

where R=OH, NH$_2$, or guanidine.

39. A compound having the formula:

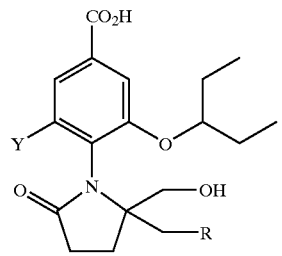

where Y is H, OH, NH$_2$, or guanidine, and R is OH, NH$_2$, or guanidine.

40. A compound having the formula:

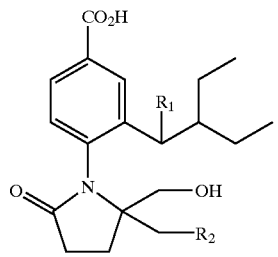

where R$_1$=H, OH, NH$_2$, or guanidine, and R$_2$=OH, NH$_2$, or guanidine.

41. A compound having the formula:

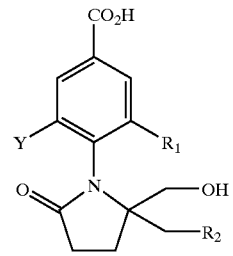

where R$_1$ is CH$_2$CH(CH$_2$CH$_3$)$_2$ or CH=C(CH$_2$CH$_3$)$_2$, R$_2$ is OH, NH$_2$, or guanidine, and Y is H, OH, NH$_2$, or guanidine.

42. A compound having the formula:

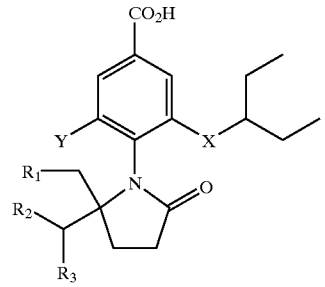

where X is CH$_2$, O, NH, CH(OH), or CH(NH$_2$), Y is H, OH, NH$_2$, or guanidine, R$_1$ is OH, NH$_2$, or guanidine, and R2 is H, OH, NH$_2$, or guanidine, and R$_3$ is a linear or branched alkyl group from 2–8 carbons.

* * * * *